US005776694A

United States Patent [19]
Sheiness et al.

[11] Patent Number: 5,776,694
[45] Date of Patent: Jul. 7, 1998

[54] DIAGNOSTIC KITS USEFUL FOR SELECTIVELY DETECTING MICROORGANISMS IN SAMPLES

[75] Inventors: Diana K. Sheiness, Bothell, Wash.; Trevor H. Adams, Buckinghamshire, England; Michael R. Stamm, Bothell, Wash.; Gerard A. Cangelosi; Theresa B. Britschgi, both of Seattle, Wash.; Connie K. Dix, Arlington, Wash.

[73] Assignee: Becton Dickinson Company, Franklin Lakes, N.J.

[21] Appl. No.: 886,999

[22] Filed: Jul. 2, 1997

Related U.S. Application Data

[60] Continuation of Ser. No. 458,319, Jun. 2, 1995, abandoned, which is a division of Ser. No. 133,598, Oct. 8, 1993, Pat. No. 5,700,636, which is a continuation-in-part of Ser. No. 896,094, May 29, 1992, abandoned, which is a continuation-in-part of Ser. No. 600,334, Oct. 19, 1990, abandoned.

[51] Int. Cl.$^6$ ............................ C12Q 1/68; C07H 21/04
[52] U.S. Cl. ............................ 435/6; 536/24.32; 422/57; 422/61; 422/104
[58] Field of Search ............... 435/6, 810; 536/24.32; 422/57, 61, 104

[56] References Cited

U.S. PATENT DOCUMENTS

| 4,652,517 | 3/1987 | Scholl et al. ............... 435/5 |
| 4,727,019 | 2/1988 | Vallirs et al. ............... 435/5 |
| 5,348,855 | 9/1994 | Dattagupta et al. ......... 435/6 |
| 5,654,418 | 8/1997 | Sheiness et al. ........ 536/24.32 |

FOREIGN PATENT DOCUMENTS

| A-0 200 381 | 11/1986 | European Pat. Off. |
| A-0 272 009 | 6/1988 | European Pat. Off. |
| A 0 288 737 | 11/1988 | European Pat. Off. |
| A-0 335 633 | 10/1989 | European Pat. Off. |
| 88/06189 WOA | 8/1988 | WIPO. |
| 8906704 | 7/1989 | WIPO. |
| WO-A-9 001 564 | 2/1990 | WIPO. |

OTHER PUBLICATIONS

Faro, et al. *Non-Specific Vaginitis or Vaginitis Undertermined Aetiology* Int. J. Tiss. Reac 1X(2), 173–177 (1987).
Rubino et al. *J. Clin. Microbiol* 29 (4), 702–706 (1991).
Sheiness et al., *J. Clin. Microbiol* 30(3), 642–648 (1992).
Dix et al., Abstr. Gen. Meet. Am. Soc. Microbiol. 92(0), Abstract 456 (1992).
Sheiness et al., *Abstr. Annu. Meet. Am. Suc. Microbiol* 89(0), Abstract 454 (1989).
Amsel, et al., *Diagnostic Criteria and Microbial a Epidemiological Associations*, Am. J. Med. 74:14–22 (Jan. 1983).
Eschenbach, et al., *Diagnosis and Clinical Manifestations Bacterial Vaginosis*, Am J. Obstet. Gynecol. 158:819–28 (Apr. 1988).
Hiller et al., *Bacterial Vaginosis*, Sexually Transmitted Diseases (K.K. Holmes, ed., 2nd Edition, 1989) 547–559.
Old, et al., *Nucleic Acid Probes and Their Applications*, Principles of Gene Manipulation (Blackwell Scientific Publications, 1989) 319–343.
Trenover, F.C., *Constructing DNA Probes For Infectious Agents*, DNA Probes For Infectious Diseases (F.C. Trenover, ed., CRC Press, Inc., Boca Raton, Florida, Nov. 1988) 1–13.
Nath et al. Res. Microbiol. 142:573–583 (1991).
Gobel et al. Journal of General Microbiolog. 133: 1969–1974 (1987).
Morse et al. in Manual of Clinical Microbiology 4th edition pp. 863–868 (1985).
West Indian Medical Journal, vol. 38, No. 3, issued Sep. 1989, P.N. Levett, "Bacterial Vaginosis", pp. 126–132, see abstract.
T. Maniatis et al., "Molecular Cloning, A Laboratory Manual" published 1982 by Cold Spring Harbor Laboratory (N.Y.), pp. 89–92, see entire document.
Journal of Bacteriology, vol. 171, No. 12, issued Dec. 1989, W.G. Weisburg et al., "A Phylogenetic Analysis of the Mycoplasmas: Basis for Their Classification", pp. 6455–6467, see entire document.

*Primary Examiner*—Kenneth R. Horlick
*Attorney, Agent, or Firm*—David W. Highet, Esq.

[57] ABSTRACT

The present invention relates, in general, to diagnostic kits for selectively detecting a prokaryotic microorganism and a eukaryotic microorganism in a sample wherein the cells of such microorganisms are lysed by combining the sample with a lysis solution and contacting the nucleic acid released from the microorganisms with selective nucleic acid probes through hybridization techniques. The present invention can be used for detecting microorganisms associated with vaginal disorders, e.g., *Gardnerella vaginalis*, *Trichomonas vaginalis* and *Candida albicans*. These kits may be used in a medical practitioner's private office or in a more structured clinical environment, such as a hospital, a commercial clinical microbiology laboratory or the like.

2 Claims, No Drawings

DIAGNOSTIC KITS USEFUL FOR SELECTIVELY DETECTING MICROORGANISMS IN SAMPLES

This application is a continuation of application Ser. No. 08/458,319, filed Jun. 2, 1995, abandoned, which is a Division of application Ser. No. 08/133,598 filed Oct. 8, 1993, U.S. Pat. No. 5,700,636, which is a continuation-in-part application of U.S. patent application Ser. No. 07/896,094, filed May 29, 1992, abandoned, which is a continuation-in-part application of U.S. patent application Ser. No. 07/600,334, filed Oct. 19, 1990, abandoned, both of which are incorporated herein by reference.

FIELD OF THE INVENTION

The present invention relates, in general, to compositions, methods and diagnostic kits useful for detecting microorganisms associated with vaginal disorders. In one aspect, the invention relates to methods for releasing intact nucleic acid from a microorganism. In another aspect, the invention relates to compositions of oligonucleotide probes for use in the detection of microorganisms associated with vaginal disorders. Methods for detection as well as diagnostic kits for the assay of these microorganisms are also disclosed.

BACKGROUND OF THE INVENTION

One of the most common reasons women seek medical treatment is for vaginal discharge or other vaginal symptoms. In women who visit their physician with vaginal complaint, approximately 40% are diagnosed as having some form of vaginitis, and 90% of these cases fall into three clinical entities: bacterial vaginosis (BV), trichomoniasis, and vulvovaginal candidiasis. (See, e.g., Sobel, "Vaginal Infections in Adult Women," Medical Clinics of North America 74:1573 (1990)). The symptoms of these three distinct diseases overlap, thus creating a need for differential diagnosis before appropriate and specific medication can be prescribed. A rapid and accurate diagnosis is especially critical in pregnant women, in whom BV and trichomoniasis are associated with premature births and low birth weight babies. Moreover, BV-positive pregnant women are predisposed to chorioamnionitis, amniotic fluid infection, and puerperal infectious morbidity. BV has also been associated with pelvic inflammatory disease, postpartum endometritis, bacteremia, salpingitis, and the like.

The term "bacterial vaginosis" was coined only a few years ago, the disease being formerly known as "leukorrhea" or "non-specific" vaginitis. Until the past decade, the cause of this syndrome was presumed to be some unidentified pathogen. A study published in 1955 suggested that *Gardnerella vaginalis* was the causative agent of BV, but this proposition was discredited by subsequent studies revealing that *G. vaginalis* was present in the vaginal secretions of 10–50% of normal women, i.e., BV-negative women. Since then it has become apparent that, unlike most diseases, BV cannot be attributed to one specific etiologic agent, but instead results from a drastic alteration of the vaginal flora. The normally present Lactobacilli become greatly reduced in number, and there is a concomitant overgrowth of several anaerobic bacteria and other microorganisms, especially *Gardnerella vaginalis* (Gv). This alteration is accompanied by an increase in vaginal pH.

The clinical "gold standard" method of diagnosing BV involves the examination of four criteria, and does not involve microbiological culture:

1) presence of clue cells (determined microscopically);
2) white or gray adherent homogeneous discharge;
3) vaginal fluid pH>4.5; and
4) fishy amine odor when vaginal fluid is mixed with 10% potassium hydroxide (KOH).

To diagnose BV, some investigators require the presence of clue cells plus two of the other three indicators, while other investigators require only that any three of the four indicators be present. In practice, physicians do not typically conduct pH and amine odor tests in their offices, nor even attempt to identify clue cells. In fact, use of the gold standard test is confined primarily to clinical studies. Identification of clue cells requires special skills, since such cells are difficult to distinguish from other microscopically observable entities. Clue cells are not microorganisms, but are vaginal epithelial cells that have been shed from the vaginal wall and to which a large number of rod-shaped bacteria have adhered. The adherent cells include *G. vaginalis*, and other anaerobic species including, for example, Mobiluncus species.

Another consistent hallmark of BV is the elevation of vaginal pH above the normal value of 4.5. Unfortunately, this highly sensitive indicator lacks specificity, as conditions other than BV can also cause an elevated vaginal pH. For example, infection with *Trichomonas vaginalis* or cervicitis can cause the vaginal pH to go up. Hence, vaginal pH by itself cannot be used to diagnose BV because such a practice would result in an unacceptable incidence of false positives.

In addition to the gold standard criteria, BV is sometimes diagnosed by assessing the shift in vaginal flora by examining Gram stained vaginal smears. This method, used primarily in research protocols, is difficult to perform and requires special training, thereby rendering it unsuitable for physician's offices. Moreover, this technique is less sensitive and less specific for BV than the gold standard method. (See, e.g., Nugent, et al., "Reliability of Diagnosing Bacterial Vaginosis Is Improved By A Standardized Method of Gram Stain," *J. Clin. Microbiol.* 29(2):297–301 (1991).

Currently, some physicians make use of a wet mount in conjunction with office vaginal examinations. A slide prepared from the patient's vaginal fluid is visually examined by the physician. When a BV-positive patient is examined by a physician practiced in making these difficult observations, such a slide will reveal an absence of the usual levels of Lactobacilli, which are large rods, and the presence of a large number of small rod-shaped bacteria, including *Gardnerella vaginalis* (Gv), Prevotella, and Mobiluncus species. The former two bacteria have straight rod shapes, while the latter bacterium exhibits a curved rod shape. Some physicians believe that clue cells may be identified through wet mount analysis, but such means of identification are not generally accepted as appropriate.

When first isolated, *G. vaginalis* was termed *Haemophilus vaginalis*. Later, *G. vaginalis* was reclassified as *Corynebacterium vaginalis*. Finally, *G. vaginalis* was placed into a new genus, Gardnerella, as it did not properly belong in either of the first two classifications. As such, some investigators have attempted to determine whether the amount of *G. vaginalis* present in a sample is indicative of BV. In doing so, they concluded that BV-positive women, on the average, have higher levels of *G. vaginalis* than BV-negative women. Considerable overlap was found to exist in the levels of *G. vaginalis* found in BV-positive and BV-negative women, however, thereby rendering the *G. vaginalis* cell level inconclusive evidence of the disease state. See, Amsel, et al., *Am. J. Med.* 74:14–22, 1983 and Eschenbach, et al., *Am. J. Obstet. Gynecol.* 158:819–28, 1988.

BV is one common cause of vaginal complaints. Other microorganisms commonly associated with such symptoms are Candida species and *Trichomonas vaginalis*. The most typical way of diagnosing candidiasis is according to symptoms, visual inspection of the vagina, and microscopic detection of the organism itself. For the wet mount, potassium hydroxide is added to dissolve epithelial cells, and the slide is examined for the presence of yeast elements, for example, pseudohyphae or budding yeast. If these measures do not yield a definitive diagnosis, the physician may order a culture. An alternative to culture method is Gram stain, which requires a trained person to analyze the results.

The classical method for the diagnosis of Trichomonas involves demonstration that the organism is present. Trichomonas is not a normal inhabitant of the vagina, and is considered a pathogen anytime it is detected. Typically, detection is done microscopically by observing protozoa with characteristic motility in vaginal secretions mixed with saline in a wet mount. Since Candida wet mounts contain potassium hydroxide, separate wet mounts must be used if one wishes to look for both of these organisms. Detection of Trichomonas depends on observation of flagellated cells of a characteristic size and shape that are in motion. Unfortunately, trichomonads quickly lose their distinctive motility upon cooling to room temperature, therefore, a microscope and trained microscopist must be available immediately after the sample is taken. Once they have lost their motility, trichomonads are practically indistinguishable from lymphocytes present on the slide. To exacerbate the challenge of microscopically detecting trichomonads is the fact that they tend to be present in low numbers.

In view of the foregoing, it is readily apparent that there are numerous disadvantages associated with the use of culture for diagnosing vaginal disorders, particularly if the woman presents with symptoms of vaginitis. The foremost disadvantage is the three to seven days required to obtain culture results. This delay can lead doctors to avoid culture altogether and, instead, to dispense medication based on a less accurate method of microscopic examination of a wet mount.

Moreover, aside from the delay in getting the results, culture can be prohibitively expensive when the syndrome can be caused by three different etiologic agents, as is the case with vaginitis. Even if a patient were willing to pay, most commercial microbiology laboratories do not offer *Trichomonas vaginauls* culture. Moreover, even when this culture is available, logistical problems arise from trying to culture three organisms from a single patient. If one swab is used and placed into the standard bacterial transport medium, the Trichomonas will not survive. This fastidious organism requires a specialized transport medium. Hence, at least two swabs must be taken. In fact, the microbiologist would prefer a separate swab for each organism to be cultured. Yet if three swabs are taken, it is not likely that all three will pick up identical samples, as the successive swabs are likely to deplete the vaginal fluid, and may even cause irritation.

In the case of *Gardnerella vaginalis* and *Candida albicans*, culture is of limited utility because these organisms can be present in the non-diseased vagina. In many instances, culture for these organisms would have diagnostic value if it were designed to yield quantitative data that could be used to identify clinically significant levels of these organisms, a procedure that involves plating serial dilutions of each sample. But, routine culture protocols do not involve plating serial dilutions to identify clinically significant levels and, thus, they determine only whether the organism is present. At best, the microbiology laboratory will inform the physician whether the growth was heavy or light. This limited information is not sufficient for the diagnosis of BV or candidiasis.

Even if a method were available for analyzing a single swab for the presence of multiple organisms, there are numerous drawbacks of culture and wet mount. As such, a biochemical test would be more economical than culturing for several different organisms. Moreover, if the test could be performed in less than an hour, the diagnosis could be completed before the patient left the doctor's office, thus enabling her to obtain the correct medication that same day.

One advantage of culture is that the organism is given a chance to multiply before being identified. However, since a swab can pick up only limited amounts of sample, a successful biochemical method would have to possess the capability of detecting very small numbers of organisms. As such, a biochemical method performed in the doctor's office would have to be able to yield results from the minuscule amount of sample present on one or two swabs. For tests that rely on detecting cytoplasmic components of the pathogenic organisms, the detection step must be preceded by efficient disruption of cell walls and membranes. Unfortunately, many pathogens of the vagina, e.g., *Candida albicans, Gardnerella vaginalis*, and Group B streptococci, are extremely difficult to lyse compared with other microorganisms. Trichomonas lyses easily, but contains potent nucleases that can easily sabotage diagnostic tests based on detection of nucleic acids.

Moreover, different methods are currently required to lyse each of these organisms. As such, the prior art has not provided a general lysis method that is effective for the simultaneous disruption and release of nucleic acids for the several pathogens of the vagina. For diagnostic tests targeted to panels rather than single microorganisms, the use of a different lysis protocol for each organism would necessitate separate swabs for each, and the separate processing would drive up the cost of the test. As a practical matter, a single lysis protocol would be far more desirable.

One potential biochemical detection method involves the use of nucleic acid hybridization. The sequence specificity embodied in nucleic acids makes it possible to differentiate virtually any two species by nucleic acid hybridization. Standard techniques for detection of specific nucleotide sequences generally employ nucleic acids that have been purified away from cellular proteins and other cellular contaminants. The most common method of purification involves lysing the cells with sodium dodecyl sulfate (SDS), digesting with proteinase K, and removing residual proteins and other molecules by extracting with organic solvents such as phenol, chloroform, and isoamylalcohol.

Endogenous nucleases released during cell solubilization can frustrate efforts to recover intact nucleic acids, particularly ribonucleic acids (RNA). While deoxyribonucleses (DNases) are easily inactivated by the addition of chelating agents to the lysis solution, ribonucleases (RNases) are far more difficult to eliminate. RNases are ubiquitous, being present even in the oil found on human hands, and they are practically indestructible. For example, the standard procedure for preparing laboratory stocks of pancreatic RNase is to boil a solution of the enzyme for 15 minutes. The purpose of this treatment is to destroy all traces of contaminating enzyme activity, since other enzymes cannot survive boiling.

Accordingly, protecting against RNase is a commonly acknowledged aspect of any standard RNA preparation technique. Sambrook, et al., which is a compendium of commonly followed laboratory practices, recommends extensive precautions to avoid RNase contamination in laboratories where RNA work is conducted. All solutions that will contact RNA are to be prepared using RNase-free glassware, autoclaved water, and chemicals reserved for work with RNA that are dispensed exclusively with baked spatulas. Besides purging laboratory reagents of RNase, RNase inhibitors are typically included in lysis solutions. These are intended to destroy endogenous RNases that generally become activated during cell lysis.

From the above descriptions, it is evident that the standard nucleic acid purification techniques are not practical for the rapid and economical detection of specific microorganisms outside of a well-equipped laboratory. Protecting against RNase is cumbersome and costly, and typical extraction procedures require the handling of caustic solvents, access to water baths, fume hoods, and centrifuges, and even the storage and disposal of hazardous wastes. The direct analysis of unfractionated solubilized microorganisms would avoid the cost and inconvenience of these purification techniques.

A minimum prerequisite for identifying microorganisms by hybridization is the release of target nucleic acids from cellular structures that otherwise would impede entry of the detection probes. Such probes consist in general of segments of nucleic acid that are complementary to sequences unique to the target organism. Once the probe has formed a hybrid with the target, the existence of that hybrid can be ascertained by activating a signal generating system that is bound to the probe.

Various impediments can block the access of hybridization probes to their target sequences, the most significant barrier being the cell wall itself. While the cell walls of many microorganisms can be effectively solubilized with guanidinium salts or with proteinase K and SDS, these methods do not effectively release readily hybridizable nucleic acids from many clinically important microorganisms, e.g., *Candida albicans* and Gram positive species. The Gram positive bacteria, which are known to be difficult to lyse, also do not efficiently yield hybridizable nucleic acids after treatment with guanidinium salts or proteinase K.

In some instances, unusual amounts of endogenous nucleases have aggravated the problem of recovering intact nucleic acids. For example, one of the few groups that has successfully extracted intact DNA from *Trichomonas vaginalis* reports that this organism is characterized by a high level of endogenous nuclease activity, and that its DNA is unusually susceptible to degradation during isolation. See, Riley, et al., *J. Clin. Microbiol.*, 30:465–472 (1992).

Moreover, the means available for lysing recalcitrant organisms are often complex and unwieldy. For example, a common method for the mechanical lysis of yeast requires the sample to be alternately vortexed with glass beads and cooled in an ice bath. The cellular extract is recovered by centrifugation after puncturing the bottom of the tube. Similarly, a Mini-Beadbeater™ has been used for lysing Mycobacterium species, where cells are ruptured by vigorous shaking with phenol and zirconium beads. See, Hurley, et al., *Journal of Clinical Microbiology*, 25:2227–2229 (1987).

The lysis of soil bacteria presents another challenge that has required drastic measures. Successful methods for their lysis have included multiple cycles of freeze-thawing, and passage through a French press, which is a high-pressure shearing device. One recent method for lysing these bacteria calls for the successive application of sonication, microwave heating, and thermal shocks. See, Picard, et al., *Applied and Environmental Microbiology*, 58:2717–2722 (1992).

Another common approach for lysis of microorganisms has involved enzymes that attack the cell walls. For example, lyticase has proven effective in lysing *Candida albicans*, while achromopeptidase, mutanolysin, or proteinase K removes cell walls from most Gram positive microorganisms. See, e.g., Kaneko, et al., *Agr. Biol Chem.*, 37:2295–2302 (1973); Bollet, et al., *Nucleic Acids Research*, 19:1955 (1991); Siegel, et al., *Infection and Immunity*, 31:808–815 (1981). However, the use of enzymes in routine detection protocols is fraught with disadvantages. Chief among these is cost, but calibration of stock solutions, lengthy incubation times, the need for low temperature storage, and limited shelf life also make the use of enzymes less than desirable for protocols involving rapid detection of microorganisms.

When the microorganisms to be detected are located in human clinical samples, additional concerns must be accommodated. For one, the presence of mucous can cause clinical samples from some sources to be viscous and unmanageable. A successful lysis procedure must disperse mucous and any other substances that may accompany the sample. Furthermore, the method of lysis must be compatible with conventional sampling techniques if they are to be widely accepted by the medical community. For example, samples from the vagina are customarily taken with a single cotton or dacron swab. Therefore, samples available for detection of vaginal pathogens normally will be limited to whatever material that can be eluted from such a swab.

In view of the foregoing, there exists a need for a simple and rapid method for releasing intact nucleic acid from both prokaryotic and eukaryotic microorganisms present in a single, biological sample. Moreover, there exists a need for a simple, fast and effective biochemical method which selectively detects the microorganisms associated with vaginitis, i.e., *Gardnerella vaginalis, Trichomonas vaginalis* and *Candida albicans*. The present invention remedies these needs by providing such methods.

SUMMARY OF THE INVENTION

In one aspect, the present invention provides a method for releasing intact nucleic acid from a microorganism, the method comprising: combining a complex biological sample containing the microorganism with a lysis solution comprising a low ionic strength buffer and a detergent, the lysis solution having a pH ranging from about 7.0 to about 12.0; and heating the combined solution to above about 65° C. for more than about five minutes to release the nucleic acid from the microorganism in the absence of mechanical force. Using this method, a number of different cells (e.g., a prokaryote and a eukaryote) present in a single, biological sample can be effectively lysed without resorting to the use of enzymes, organic solvents, glass beads, or bulky machinery (e.g., a French press).

The present invention also provides a method and kit for selectively detecting a prokaryotic microorganism and a eukaryotic microorganism in a single, complex biological sample, the method comprising: (a) lysing the cells of the prokaryotic microorganism and the eukaryotic microorganism by combining the sample with a lysis solution, thereby releasing nucleic acid from the microorganisms; (b) contacting the nucleic acid released from the microorganisms, under hybridizing conditions, with an oligonucleotide capture probe that selectively hybridizes to the nucleic acid of the prokaryotic microorganism and an oligonucleotide capture probe that selectively hybridizes to the nucleic acid of the eukaryotic microorganism to form a prokaryotic microorganism-capture probe hybridization complex and a eukaryotic microorganism-capture probe hybridization complex. respectively; and (c) detecting the hybridization complexes as an indication of the presence of the prokaryotic microorganism and the eukaryotic microorganism in the sample.

Moreover, in another aspect of the present invention, a method and kit are provided for selectively detecting a Group I microorganism selected from the group consisting of gram positive bacteria, and at least one other Group II microorganism selected from the group consisting of yeasts, protozoa, mycoplasmas and gram negative bacteria in a single, complex biological sample, the method comprising: (a) lysing the cells of a Group I and a Group II microorganisms by combining the sample with a lysis solution, thereby intact nucleic acid from the microorganisms; (b) contacting the nucleic acid released from the microorganisms, under hybridizing conditions, with an oligonucleotide capture probe that selectively hybridizes to the nucleic acid of the Group I microorganism and an oligonucleotide capture probe that selectively hybridizes to the nucleic acid of the Group II microorganism to form a Group I microorganism-capture probe hybridization complex and a Group II microorganism-capture probe hybridization complex, respectively; and (c) detecting the hybridization complexes as an indication of the presence of the Group I microorganism and the Group II microorganism in the sample.

Using the methods of the present invention, the following exemplary organisms can be selectively detected in a single, biological sample: *Gardnerella vaginalis*, *Trichomonas vaginalis*, Candida species (e.g., *C. albicans*, *C. glabrata*, *C. kefyr*, *C. krusei*, *C. parapsilosis* and *C. tropicalis*), Group B Streptococci, *Prevotella bivia*, *Ureaplasma urealyticum*, Mobiluncus species, Mycoplasma species, *Neisseria gonorrhea*, Chlamydia species and Enterobacteriaceae.

In a further aspect, the present invention provides a method for determining whether a patient is afflicted with bacterial vaginosis (BV) that is fast, accurate, and does not require an individual skilled in identifying clue cells, evaluating wet mounts or the like to assess the results. The method comprising: (a) determining the pH of a vaginal sample obtained from the patient; (b) detecting the *Gardnerella vaginalis* (Gv) cell level in the vaginal sample in a time period of about 6 hours or less; and (c) determining that the patient is BV-positive if the pH value of the vaginal sample is greater than about 4.5 and the Gv cell level of the vaginal sample is greater than or equal to a critical Gv cell number.

The present invention also provides pharmaceutical and diagnostic kits for use in the methods of the present invention. For example, the present invention provides a diagnostic kit for selectively detecting a prokaryotic microorganism and a eukaryotic microorganism in a single, complex biological sample, the kit comprising: (a) a dipstick comprising a nonporous solid support having attached thereto at least two capture oligonucleotide-coated beads, wherein the first bead selectively hybridizes to the nucleic acid of a prokaryotic microorganism and the second bead selectively hybridizes to the nucleic acid of a eukaryotic microorganism to form a prokaryotic microorganism-capture probe hybridization complex and a eukaryotic microorganism-capture probe hybridization complex, respectively; and (b) a container including at least two signal oligonucleotides, wherein the first signal oligonucleotide hybridizes to the prokaryotic microorganism and the second signal oligonucleotide hybridizes to the eukaryotic microorganism. Additionally, the present invention a diagnostic kit for determining whether a patient is afflicted with bacterial vaginosis (BV), the kit comprising: (a) a first indicator capable of indicating a pH greater than about 4.5; and (b) a second indicator capable of indicating a Gv cell level greater than or equal to a critical Gv cell number.

Other advantages, objects, features and embodiments of the present invention will become apparent from the detailed description which follows.

DETAILED DESCRIPTION OF THE INVENTION AND PREFERRED EMBODIMENT

The present invention provides a method for releasing intact nucleic acid from a microorganism, the method comprising: combining a complex biological sample containing the microorganism with a lysis solution comprising a low ionic strength buffer and a detergent, the lysis solution having a pH ranging from about 7.0 to about 12.0; and heating the combined solution to above about 65° C. for more than about five minutes to release the nucleic acid from the microorganism, wherein the lysis solution is capable of releasing intact nucleic acid from the microorganism in the absence of mechanical force.

As used herein, the term "nucleic acid" refers to a deoxyribonucleotide or ribonucleotide polymer in either single-stranded or double-stranded form and, unless otherwise limited, encompasses known analogs of natural nucleotides which can function in a similar manner as naturally occurring nucleotides. As used herein, the term "intact" nucleic acid refers to hybridizable nucleic acid, i.e., nucleic acid of a sufficient length such that it is capable of hybridizing to an oligonucleotide probe. The term "complex biological sample" is used herein to refer to a biological mixture, e.g., vaginal fluid, of nucleic acid (RNA and/or DNA) and non-nucleic acid. Such a complex biological mixture includes a wide range of eukaryotic and prokaryotic cells.

Moreover, as used herein, the term "microorganism" refers to both prokaryotic and eukaryotic microorganisms. The significant differences between eukaryotic and prokaryotic cells would lead one to believe that a simple, universal method for releasing intact nucleic acid from a microorganism would not work well for both kinds of cell, especially the difficult-to-lyse yeast and the gram-positive bacteria. It has been discovered, however, that the above lysis method works well for releasing intact nucleic acid from both eukaryotic and prokaryotic microorganisms, including, for example, gram-positive bacteria and yeast.

Eukaryotic cells are found in all vertebrates, protozoa, and fungi, while bacteria exhibit the more primitive prokaryotic cell type. Both eukaryotic and prokaryotic cells are surrounded by a lipid bilayer that selectively regulates which molecules may enter or leave the cell. The lipid bilayer can be ruptured or solubilized by a variety of means, such as suspending the cells in hypotonic solutions, or treating them with organic solvents, although such means do not necessarily inactivate nucleases.

In addition to the lipid bilayer, bacteria and some types of primitive eukaryotic cells are encased by a rigid cell wall that surrounds the entire cell, including the plasma membrane itself. In bacteria, this tough protective coat is composed of a carbohydrate matrix cross-linked by short polypeptide units. (See, Raven and Johnson, *Biology*, p. 87, Times Mirror/Mosby College Publishing, 2nd ed., 1989.) No eukaryotes possess cell walls with a chemical composition of this kind. The most common methods for lysing bacteria without organic solvents involve treating the bacteria with lytic enzymes. Lysozyme and mutanolysin are commonly used to lyse gram-negative and gram-positive bacteria, respectively, but these enzymes are totally ineffective in lysing eukaryotic cells.

Yeast, which is a type of fungus, also possesses cell walls, but these differ in composition from those of bacterial cell walls. Cell walls of yeast rely primarily on β-1,3-glucans for their rigidity. Yeast cell walls are often stabilized by disulfide bonds that can be disrupted with mild reducing agents such as β-mercaptoethanol. A number of enzymes, including lyticase, chitinase, and Novozym™, are effective in lysing some strains of yeast. The lytic activity of lyticase is attributable to both a β-1,3,-glucanase and a protease and lyses yeast only in the presence of a reducing agent. (See, Scott and Schekman, *J. Bacteriol.* 142:414-423 (1980), for a description of lyticase). Novozym™, sold by Novo BioLabs, includes glucanase, proteinase, and chitinase activities. In experiments performed by Applicants, lyticase, but not Novozymn™ or chitinase, was effective in lysing *Candida albicans*.

Bacteria can be differentiated to some extent according to the composition of their cell walls. Bacteria are commonly classified according to whether or not they take up color during a procedure known as the Gram stain. Cell that incorporate the stain, known as "gram-positive" bacteria, have a single, thick cell wall that retains the stain and results in their appearing purple under the microscope. Gram-negative bacteria have evolved thinner and more complex cell walls that do not retain the stain. Gram-positive and gram-negative bacteria often differ in their susceptibility to different kinds of antibiotics as well as in their susceptibility to various lysis protocols.

Gram-positive bacteria have proven to be exceptionally difficult to lyse compared with gram-negative bacteria. For example, gram-positive bacteria are resistant to the inexpensive egg white lysozyme commonly used to lyse gram-negative microbes (Siegel, et al., *Infec. and Immun.* 31:808-815 (1981)). As previously discussed, investigators have often resorted to the use of expensive enzymes to lyse gram-positive bacteria.

Of particular interest is the simultaneous lysis of several pathogenic microorganisms that infect the human vagina. These microorganisms include, but are not limited to, *Gardnerella vaginalis*, *Prevotelia bivia*, *Trichomonas vaginalis*, *Candida albicans*, and several species of Group B streptococci. Of these, several are difficult to lyse by conventional means. *Trichomonas vaginalis* presents a problem because of its reportedly high endogenous level of nucleases. *Candida albicans* and the Group B streptococci are problematic because of their relatively impervious cell walls. Furthermore, the rapid and economical non-enzymatic lysis of both eukaryotic and prokaryotic organisms in the same reaction mix is a challenge not met by any method in the existing art.

As such, a new approach has been discovered that is effective for lysing a number of different kinds of cells without resorting to the use of enzymes, organic solvents, glass beads, or bulky machinery. As previously mentioned, the lysis method of the present invention consists of combining a complex biological sample containing the microorganism to be lysed with a lysis solution comprising a low ionic strength buffer and a detergent, the lysis solution having a pH ranging from about 7.0 to about 12.0; and heating the combined solution to above about 65° C. for more than about five minutes to release the nucleic acid from the microorganism, wherein the lysis solution is capable of releasing intact nucleic acid from the microorganism in the absence of mechanical force.

In this lysis method, the lysis solution contains a buffer having an ionic strength ranging from about 15 mM to about 150 mM. Suitable buffers which can be used for maintaining the pH of the lysis solution include, but are not limited to, the following: brucine tetrahydrate, 4-(2-hydroxyethyl)-1-piperazinepropane sulfonic acid ("EPPS"), tris (hydroxymethyl)aminomethane ("TRIS"), N-tris (hydroxymethyl)methylglycine ("TRICINE"), glycinamide, N,N-bis(2-hydroxyethyl)glycine ("BICINE"), N-tris (hydroxymethyl)methyl-2-aminopropane sulfonic acid ("TAPS"), N-glycyl-glycine, histidine, boric acid, pyrophosphoric acid, ethanolamine, glycine, trimethylamine, cyclopentanetetra-1,2,3,4-carboxylic acid, carbonic acid, 3-cyclohexylamino-1-propanesulfonic acid ("CAPS"), EDTA, methylamine, dimethylamine, ethylamine, triethylamine, diethylamine, ascorbic acid, and phosphoric acid.

Detergents suitable for use in the lysis method of the present invention include, but are not limited to, the following: anionic detergents, cationic detergents, zwitterionic detergents and non-ionic detergents. Anionic detergents include, but are not limited to, the sodium salts of caprylic acid, cholic acid, 1-decanesulfonic acid, deoxycholic acid, glycocholic acid, glycodeoxycholic acid, lauryl sulfate ("SDS"), N-lauroylsarcosine, taurocholic acid, taurodeoxycholic acid. Cationic detergents include, but not limited to, cetylpyridinium chloride, dodecyltrimethylammonium bromide, hexadecyltrimethylammonium bromide, and tetradecyltrimethylammonium bromide. Zwitterionic detergents include, but are not limited to, CHAPS and CHAPSO. Non-ionic detergent including, but not limited to, n-decyl β-D-glucopyranoside, digitonin, n-docedyl β-D-glucopyranoside, n-dodecyl β-D-maltoside, n-heptyl β-D-glucopyranoside, n-octyl β-D-glucopyranoside, n-octyl α-D-glucopyranoside, nonidet P-40, n-nonyl β-D-glucopyranoside, and Triton X-100.

Additionally, the lysis solution can include a chelating agent (e.g., EDTA) and/or a preservative (e.g., ProClin®). In contrast to methods in the prior art, no enzymes or ribonuclease inhibitors are required in the lysis solution of the present invention. As such, a presently preferred formulation of the lysis solution used in the disclosed method for releasing intact nucleic acid from a microorganism is as follows: 91 mM N-tris(hydroxy-methyl)aminomethane; 0.5% sodium dodecyl sulfate; 5.0% N-lauroyl-sarcosine (optional); 10 mM EDTA, and 0.1% ProClin® 150.

The pH optima of the lysis solution will depend upon which microorganism(s) is being lysed. In the present format, the pH optima has been determined for a number of microorganisms of interest, including the bacteria *Gardnerella vaginalis*, *Prevotella bivia*, and Group B streptococci; the protozoan *Trichomonas vaginalis*; and the yeast *Candida albicans*. For *Candida albicans*, the optimal pH ranges from a pH of about 10 to about 11.5, but substantial lysis was observed across the entire pH range from about 6.0 to about 11.5. Likewise, *Trichomonas vaginalis* lysed well across the this entire range of pHs, with slightly better results at a pH above about 8.5. *Gardnerella vaginalis* lysed well across the entire range, with a slight decrease in assay signal at pHs above 9.5. The optimal pH for lysing Group B streptococci was a pH of about 6.0 to abut 8.0, but a substantial amount of lysis was seen at pHs ranging from about 7.0 to about 12.0.

It will be readily apparent to those of skill in the art that the pH optima for other microorganisms can readily be determined. For example, the lysis conditions for Group B streptococci were optimized using the following procedure.

As a "gold standard" for comparison with the test samples set forth below, suspensions containing known numbers of freshly-grown bacteria were lysed with a solution containing about 1 mg/Ml mutanolysin, 2 mg/mL achromopeptidase, 2 mg/mL lysozyme, 2 mg/mL lipase-PN, and 10 mg/mL 20-T Zymolase. After incubating for about five minutes at 37° C., proteinase K and SDS were added to final concentrations of about 1 mg/ml, and 1.5%, respectively. This mixture was incubated for an additional five minutes at 60° C. This treatment was designed to ensure complete lysis by inclusion of all of the enzymes shown previously to effect lysis of Group B streptococci.

For the test samples, known numbers of freshly-grown bacteria were placed in a number of test vials and the following lysis solution was added to each sample: 91 mM N-tris(hydroxy-methyl)aminomethane; 0.5% sodium dodecyl sulfate; 5.0% N-lauroyl-sarcosine (optional); 10 mM EDTA, and 0.1% ProClin® 150. Holding all other factors the same, the pH of the lysis solution was varied over a pH ranging from about 5.0 to about 12.0. Similarly, holding all factors the same, the temperature of the lysis solution was varied over a wide range. The optimal lysis conditions for Group B streptococci were assessed by comparing the amount of ribosomal RNA detected in each test sample with the amount of ribosomal RNA detected in the gold standard lysis mixture. In doing so, it was determined that Group B streptococci became completely lysed at a temperature of about 85° C., but substantial lysis was seen at temperatures exceeding 65° C. The optimal pH for lysing Group B streptococci ranges from a pH of about 6.0 to about 8.0, but a substantial amount of lysis was seen at pH's ranging from about 7.0 to about 12.0. It will be readily apparent to those of skill that the pH optima for any microorganism can be determined using a procedure similar to that used for Group B streptococci.

In a presently preferred embodiment of the lysis method, the combined solution (i.e., the lysis solution and target microorganism) is heated to a temperature above about 65° C. for a period of about five to about ten minutes. More preferably, the combined solution is heated to a temperature ranging from about 75° C. to about 95° C. Even more preferably, the combined solution is heated to a temperature of about 85° C. If the lysis temperature exceeds 95° C., little or no nucleic acid can be detected in the subsequent assays. As such, in contrast to previously used lysis methods, the use of enzymes, organic solvents, glass beads, or bulky machinery are not required in the lysis methods of the present invention.

As a result of this ability to lysis multiple microorganisms in a single, complex biological sample, assays of any combination of microorganisms discussed above can be conducted in the same reaction mixture, thereby making it possible to devise diagnostic assays for different microorganisms that may be present in the same complex biological sample, e.g., the same patient sample. This approach is useful for devising assays for pathogens all of which are associated with the same clinical symptoms. For example, the vaginitis organisms *Gardnerella vaginalis*, *Candida albicans*, and *Trichomonas vaginalis* can all be in a single sample if the microorganisms are first lysed to release their nucleic acid using the lysis method of the present invention. As such, a single sample from pregnant women can be assessed for the presence of multiple organisms which are known to cause premature birth. For example, a prenatal assay panel can include *Trichomonas vaginalis*, *Prevotella bivia*, *Gardnerella vaginalis*, and Group B streptococci or, a subset thereof. As this lysis method works on such a great variety of microorganisms, a wide variety of combinations of organisms can be assayed by analyzing single patient samples from any part of the body.

As such, in another aspect of the present invention, a method and kit are provided for selectively detecting a prokaryotic microorganism and a eukaryotic microorganism in a single, complex biological sample, the method comprising: (a) lysing the cells of the prokaryotic microorganism and the eukaryotic microorganism by combining the sample with a lysis solution, thereby releasing nucleic acid from the microorganisms; (b) contacting the nucleic acid released from the microorganisms, under hybridizing conditions, with an oligonucleotide capture probe that selectively hybridizes to the nucleic acid of the prokaryotic microorganism and an oligonucleotide capture probe that selectively hybridizes to the nucleic acid of the eukaryotic microorganism to form a prokaryotic microorganism-capture probe hybridization complex and a eukaryotic microorganism-capture probe hybridization complex, respectively; and (c) detecting the hybridization complexes as an indication of the presence of the prokaryotic microorganism and the eukaryotic microorganism in the sample.

In accordance with this method and kit of the present invention, a prokaryotic microorganism in combination with a eukaryotic microorganism can be selectively detected. Additionally, multiple prokaryotic microorganisms in combination with multiple eukaryotic microorganisms can be selectively detected. Moreover, a single prokaryotic microorganism in combination with multiple eukaryotic microorganisms, or vice-versa, can be selectively detected.

In a presently preferred embodiment, the prokaryotic microorganism is *Gardnerella vaginalis*, whereas the eukaryotic microorganism includes, but is not limited to, *Trichomonas vaginalis* and *Candida albicans*. In another preferred embodiment, *Gardnerella vaginalis*, *Trichomonas vaginalis* and *Candida albicans* are all selectively detected. In a further preferred embodiment, in addition to *Gardnerella vaginalis*, *Trichomonas vaginalis* and *Candida albicans*, Group B Streptococci, *Prevotella bivia*, *Ureaplasma urealyticum*, *Mobiluncus* species, *Mycoplasma* species, *Neisseria gonorrhea*, Enterobacteriaceae and Chlamydia species are also selectively detected.

The cells of the prokaryotic and eukaryotic microorganisms of interest are lysed by combining the single, complex biological sample containing the microorganisms with a lysis solution, thereby releasing nucleic acid, i.e., the target nucleic acid, from the microorganisms. The previous discussion pertaining to the method for releasing intact nucleic acid from a microorganism is fully applicable to the method at hand. As such, the cells of the various microorganisms are lysed by combining the complex biological sample containing the microorganisms with a lysis solution comprising a low ionic strength buffer and a detergent, the lysis solution having a pH ranging from about 7.0 to about 12.0; and heating the combined solution to above about 65° C. for more than about five minutes to release the nucleic acid from the microorganisms in the absence of mechanical force. Moreover, as previously stated, the term "complex biological sample" is used herein to refer to a biological mixture, e.g., vaginal fluid, of nucleic acid (RNA and/or DNA) and non-nucleic acid. Such a complex biological mixture includes a wide range of eukaryotic and prokaryotic cells.

Once the nucleic acid is released from the cells of the microorganisms of interest, the specific nucleic acid sequences of interest, i.e., the target nucleic acid sequences, are detected and identified through the use of nucleic acid hybridization assays. Hybridization is based upon the pairing of complementary nucleic acid strands. When complementary single stranded nucleic acids are incubated in appropriate buffer solutions and conditions, complementary nucleotide sequences pair to form stable, double stranded molecules (i.e., the sequences hybridize to form a hybridization complex or duplex). The particular hybridization technique employed is not essential to the method of the present invention, and one of ordinary skill in the art will appreciate the variety of such techniques. Hybridization techniques are generally described in Hames, et al. (eds.), "Nucleic Acid Hybridization, A Practical Approach", IRL Press, New York, 1985. As improvements are made in hybridization techniques, they will be readily applicable to the present invention.

Sandwich assays are preferably employed in the present method. A primary component of a sandwich type assay is a solid support. The solid support has adsorbed to it or covalently coupled to it at least one, preferably more than one, oligonucleotide capture probe which is complementary to the target nucleic acid being detected and thus, it is capable of selectively or specifically hybridizing to the nucleic acid of the target microorganism. The complex biological sample suspected of containing the microorganism of interest, i.e., the target nucleic acid, is contacted with the solid support in a hybridization medium. If present, the target nucleic acid being detected is sequestered (i.e., captured) on the solid support (e.g., a bead or microtiter plate) by hybridizing (i.e., pairing of complementary bases) to the oligonucleotide capture probe covalently immobilized on the surface of the solid support to form a microorganism-oligonucleotide capture probe hybridization complex or duplex.

In such hybridization assays, the target nucleic acid (or amplicon thereof) is the nucleotide sequence of deoxyribonucleic acid (DNA), ribonucleic acid (RNA) or ribosomal nucleic acid (rRNA) whose presence is of interest and whose presence or absence is to be detected. The target nucleic acid may be provided in a complex biological mixture of nucleic acid (DNA, RNA and/or rRNA) and non-nucleic acid. In the present invention, the target nucleic acids of primary preference are RNA molecules and, in particular, open regions of rRNA which have minimal secondary or tertiary interactions with adjacent nucleotides, such as on the 16S or 23S rRNA. If target nucleic acids of choice are double stranded or otherwise have significant secondary or tertiary structure, they may need to be heated prior to hybridization. In this case, heating may occur prior to or after the introduction of the nucleic acids into the hybridization medium.

Once the target nucleic acid has undergone hybridization with the capture oligonucleotide probe, the microorganism-oligonucleotide capture probe hybridization complex, if present, must be detected. In a preferred embodiment, the microorganism-capture probe hybridization complex is detected by the use of a signal oligonucleotide which is not complementary to the capture probe and which selectively hybridizes to the nucleic acid of the target microorganism. To be effective, the signal probe cannot hybridize to the capture probe. As such, a second hybridization with a signal oligonucleotide probe is performed. In this manner, the presence of captured target nucleic acid is detected or confirmed, and the amount of captured target nucleic acid may be quantified. Alternatively, this detection step can be performed simultaneously with the capture of the target nucleic acid by including the signal oligonucleotide probe within, for example, the initial hybridization solution. This results in a "sandwich" of the oligonucleotide capture pro-be:target nucleic acid:signal oligonucleotide probe, constituting a sandwich assay. The solid support is then washed to remove unhybridized material, and the signal oligonucleotide probe is detected in a manner consistent with the detectable characteristics of the signal oligonucleotide probe.

It will be understood by those of skill that the sensitivity of the hybridization assays may be enhanced through the use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q-Beta Replicase systems. When such amplification methods are used to enhance the sensitivity of the hybridization assay, the amplicon of the target nucleic acid is subsequently detected in the hybridization assay.

As used herein, the term "oligonucleotide" refers to a short nucleic acid sequence that is approximately 6 to 150 bases in length. Such oligonucleotides can be used as capture or signal probes in hybridization assays, and are preferably chemically synthesized using commercially available methods and equipment. For example, the solid phase phosphoramidite method can be used to produce short probes of between 6 and 100 bases having a molecular weight of less than 16,000 daltons. See, Caruthers, et al., *Cold Spring Harbour Symp. Quant. Biol.* 47:411–18, 1982; and Adams, et al., *J. Am. Chem. Soc.* 105:661, 1983, for the synthesis of oligonucleotides, both of which are incorporated herein by reference.

Preferred capture oligonucleotides are designed for both target specificity and duplex (i.e., hybridization-complex) formation with target nucleic acid in a solid phase sandwich assay format. The latter characteristic is particularly important when the target is ribosomal RNA. Moreover, preferred capture oligonucleotides are designed so that they comprise a segment of nucleic acid that selectively hybridizes to regions of ribosomal RNA of the microorganism having minimal secondary or tertiary interactions with adjacent nucleotides (i.e., open regions), the probes substantially binding to only to open regions. By "substantially binding," it is meant that the probes do not comprise significant sequences that bind to regions that are available for hybridization only after heating, that is, regions with significant secondary and tertiary structure (i.e., closed regions). As such, one of the advantages of such capture probes is that the hybridization can be carried out without the additional step of denaturing the sample nucleic acid.

Moreover, capture oligonucleotides may be designed for a range of specificities. That is, capture oligonucleotides may be specific for prokaryotic target nucleic acid or eukaryotic target nucleic acid, or may selectively hybridize with the genus and/or species of the target. As described herein, the design of capture oligonucleotides and signal oligonucleotides and, the selection of lysis conditions, concentration of capture oligonucleotide on a bead, hybridization conditions, signal/detection systems and conditions, and combinations thereof may impact the sensitivity and specificity of detection of a particular panel of microorganisms. However, one skilled in the art of nucleic acid sandwich hybridization assays can determine modifications or adjustments of these parameters that optimize simultaneous detection of a particular panel of target microorganisms.

When synthesizing an oligonucleotide probe for detection of a specific target nucleic acid, such as *G. vaginalis* RNA, DNA or the like, the choice of nucleotide sequence will determine the specificity of tests using such probes. For example, by comparing nucleic acid sequences from *G. vaginalis* isolates, one can design an oligonucleotide sequence for *G. vaginalis* detection that is either type-specific, species-specific or genus-specific. Comparisons of nucleic acid regions and sequences can be conducted using commercially available computer programs such as the MicroGenie Program, sold by Beckman Instruments (Palo Alto, Calif.). Some programs are limited in that only two sequences can be compared at a time and all nucleotides are given equal importance. A more complex comparison can be made, but a more complex computer (e.g., a Cray computer) is required. See, e.g., Waterman, "Multiple Sequence Alignment by Consensus," *Nuc. Acids Res.* 14:9095–9102 (1986). The preferred method for the development of a species-specific probe requires alignment of multiple sequences and the identification of conserved blocks. Probes are then designed to include maximum diversity (e.g., insertions or deletions instead of transitions). The probes may be either DNA or RNA, although DNA probes are preferred because they can be chemically synthesized.

Oligonucleotide capture probes useful in the present invention selectively hybridize with a nucleic acid sequence specific for *G. vaginalis*; *G. vaginalis* 16S rRNA is a preferred *G. vaginalis* nucleic acid target for this purpose, because it is present in several thousand copies per cell. However, oligonucleotides complementary to sequences in the *G. vaginalis* genome or in *G. vaginalis* plasmids may also be employed. In addition, oligonucleotide probes that selectively hybridize with nucleic acid sequences specific for Candida species (e.g., *C. albicans, C. glabrata, C. kefyr, C. krusei, C. parapsilosis* and *C. tropicalis*), Group B Streptococci, *Prevotella bivia, Ureaplasma urealyticum*, Mobiluncus species, Mycoplasma species, *Neisseria gonorrhea*, Chlamydia species, Enterobacteriaceae and *Trichomonas vaginalis* are described. Exemplary oligonucleotide probes useful in the present methods and kits are provided in the "Materials" section of this description and in Example 7.

The preferred capture oligonucleotides for use in the present invention are synthetic oligonucleotides from about 6 to about 150 bases in length. A spacer (linker) arm (i.e., a chemical moiety that extends or links other chemical groups, and preferably is a carbon chain containing from about 2 to about 12 carbon atoms and, more preferably, about 6 carbon atoms) containing a blocked amine group can be coupled during oligonucleotide synthesis using conventional chemistry to the 5'-hydroxyl group of an oligonucleotide. A primary amine is the preferred group for reaction with monofunctional or multifunctional reagents, and its attachment via a hexyl arm is preferred. Reagents useful for the attachment of spacer arms terminating in a primary amine are commercially available. Starting materials suitable for use in accordance with the present invention are known in the art and are described in PCT 86/01290; *Nucl. Acids Res.* 15:3131 (1987); *Nuc. Acids Res.* 14:7985, all of which are incorporated herein by reference.

Preferably, an oligonucleotide possessing a 5'-terminal structure, such as

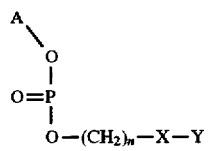

is employed, wherein n is 1–12, inclusive (n=6 preferred); X is —NH— or —NHC:O($CH_2$)$_m$NH—, wherein m is 2–12, inclusive; Y is 4,6-dichlorotriazine (preferred) or a thiol (sulfhydryl)-reactive moiety; A is an oligonucleotide, ranging from about 9 to about 100 bases, preferably from about 15 to about 30 bases, with only the 5'-hydroxyl oligonucleotide moiety requiring modification for attachment.

Alternatively, the oligonucleotide can be modified at the 3'-end with a spacer arm containing a blocked amine group. This can be accomplished by conducting DNA synthesis on a solid support containing a conjugated ribonucleotide. After removal from the solid support, a DNA oligonucleotide is obtained that contains a single 3'-terminal ribonucleotide. This can be modified with a spacer arm containing a nucleophilic amine by, for example, oxidizing the ribonucleotide cis-glycol with periodate; treating oligonucleotide so modified with, for example, butane diamine to form a Schiff base; and treating with sodium borohydride or cyanoborohydride to form a stable reduced Schiff base derivative in which one of the amines is left free for subsequent conjugation.

The designed oligonucleotides are then activated with a monofunctional or multifunctional reagent. "Activated oligonucleotides" refer, in general, to oligonucleotides that have been reacted with a chemical compound and rendered chemically active. As used herein, the term "activatable" refers to the potential of a moiety to become chemically reactive. Exemplary multifunctional reagents include, but are not limited to, homotrifunctional, heterotrifunctional, homobifunctional, and heterobifunctional reagents.

Activated oligonucleotides may be linked to polymer-coated solid supports. As used herein, the term "solid support" refers to any surface that is transferable from solution to solution or forms a structure for conducting oligonucleotide-based assays, and includes beads, membranes, microtiter wells, strings, plastic strips, or any surface onto which nucleic acid probes may be immobilized. As used herein, the term "bead" encompasses any type of solid or hollow sphere, ball, bearing, cylinder, or other similar configuration composed of plastic, ceramic, metal, or polymeric material onto which a nucleic acid can be covalently immobilized. As such, the term also includes string or strings. Preferably, a bead that is spherical in shape is employed in the present compositions, and a preferred diameter range for such beads is from about 0.01 inch to about 0.5 inch, more preferably from about 0.06 inch to about 0.09 inch (corresponding to commercially available 3/32 inch nylon beads), and most preferably about 0.09 inch (corresponding to commercially available 3/32 inch nylon beads). Additionally, it is preferred that the beads are unpolished or, if polished, roughened before treating with an alkylating agent.

In a preferred embodiment of the present invention, a nylon bead (or beads or any composition or structure of nylon) is activated by treating the bead with an alkylating agent. Alkylating agents react with amides present in the nylon polymer to form reactive imidate esters. Preferred alkylating agents include, but are not limited to, dialkyl sulfates, alkyl triflates, alkyl-diphenyl sulfonium salts, alkyl perchlorates, and, more preferably, trialkyloxonium salts.

Exemplary trialkyl-oxonium salts useful in the present invention include lower alkyl salts, such as, for example, trimethyloxonium and triethyl-oxonium salts. Exemplary salt counterions are hexachloroantimonate, hexafluorophosphate, and tetrafluoroborate, with the last named counterion being preferred.

An alkylating agent solvent that does not dissolve nylon or render nylon tacky during the alkylation procedure is preferably employed in activating the preferred nylon solid support useful in the diagnostic methods and kits of the present invention. Non-nucleophilic organic solvents, such as dichloromethane, dimethylsulfoxide, tetrahydrofuran, and others, are exemplary solvents that may be employed for this purpose. N-methyl-pyrrolidone is preferred because it is a solvent that supports alkylation.

The resulting bead surface imidate esters are then reacted under suitable conditions with an amine-containing polymer, whereby amidine residues are formed. Any primary or secondary amine-containing polymer can be employed to form amidine residues, thus covalently immobilizing the polymer onto the surface of the bead. Poly (ethylene-imine), polyallylamine, and polyvinylamine are preferred examples. The preferred solvent used to dissolve the polymer during the conjugation of the polymer to the activated nylon bead is N-methyl-pyrrolidone.

Alternatively, nylon can also be partially hydrolyzed to yield reactive amine or carboxyl groups (capable of subsequently reacting with amine- or carboxyl- containing polymers). In this manner, an activated solid support coated with reactive moieties may be produced.

Activated oligonucleotides may be linked to such polymer-coated solid supports according to the following chemistries. In general, there are two modes by which the oligonucleotide can be covalently attached to the polymer at this point. An amine-tailed oligonucleotide can be activated with a monofunctional or multifunctional reagent, for example cyanuric chloride whereby an alkylamino dichlorotriazine is formed, which is then reactive toward the amine-containing polymer. Alternatively, the polymer on the surface of the bead can be activated with a reagent, preferably the homotrifunctional reagent cyanuric chloride, which is then reactive toward the amine-tailed or amine-derived oligonucleotide.

Although cyanuric chloride, a homotrifunctional reagent, is preferred, other activating reagents can be used. For example, N-succinimidyl-4-(iodoacetamido)-benzoate (SIAB) is a suitable heterobifunctional reagent, and disuccinimidyl suberate is a suitable homobifunctional reagent. If solid support carboxyl groups are involved, the heterobifunctional reagent 1-ethyl-3-(dimethyl-aminopropyl)-carbodiimide can be used. Other similar monofunctional and multifunctional (heteromultifunctional and homomultifunctional) reagents are suitable for use in the practice of the present invention.

The oligonucleotide activation and linking chemistries result in the selective activation of an amino group on an oligonucleotide, without modification of any of the purine and pyrimidine bases of the oligonucleotide. Specifically, the preferred chemistry employs cyanuric chloride (2,4,6,-trichloro-1,3,5,-triazine). Oligonucleotides possessing a 5' or 3' tethered (via a hexyl arm) nucleophilic amine moiety (or internal aminoalkyl groups substituted on pyrimidine or purine bases) are reacted with an excess, preferably 50- to 200-fold, of recrystallized cyanuric chloride at, preferably, 19°–25° C. a part organic solvent, such as N-methyl pyrrolidone, for 1 to 2 hours.

The unreacted cyanuric chloride can be removed by exclusion chromatography or ultrafiltration. The treated solid support and activated oligonucleotide are then conjugated. Specifically, they are mixed together and preferably incubated at from about 20° to 50° C. for about 1 to 24 hours. The residual (unreacted) amines on the bead surface can be capped (blocked) with an agent, such as succinic anhydride, preferably in N-methyl pyrrolidone in the presence of an appropriate base, such as sodium borate, to render the surface compatible (negatively charged) for nucleic acid hybridization. It should be noted that the solid support may be chemically modified to produce a positive, negative, or neutral surface charge.

Dipsticks are preferably employed in the methods and kits of the present invention. For example, the present invention provides a kit for selectively detecting a prokaryotic microorganism and a eukaryotic microorganism in a single, complex biological sample, the kit comprising: (a) a dipstick comprising a nonporous solid support having attached thereto at least two capture oligonucleotide-coated beads, wherein the first bead selectively hybridizes to the nucleic acid of the prokaryotic microorganism and the second bead selectively hybridizes to the nucleic acid of the eukaryotic microorganism to form a prokaryotic microorganism-capture probe hybridization complex and a eukaryotic microorganism-capture probe hybridization complex, respectively ; and (b) a container including at least two signal oligonucleotides, wherein the first signal oligonucleotide hybridizes to the nucleic acid of the prokaryotic microorganism and the second signal oligonucleotide hybridizes to the nucleic acid of the eukaryotic microorganism.

Dipsticks having utility in nucleic acid hybridizations include a nonporous bead support and a means for attaching a bead thereto. Nonporous bead supports are known in the art. An example of bead attachment to a nonporous bead support involves a perforation or perforations (or a depression or depressions) in the nonporous bead support, wherein beads can be attached. Preferably, perforations are employed and the beads are attached by pressure fit within the circumference of the such perforations. Such a pressure fit can occur if, for example, the circumference of the perforation (or depression) is slightly less than the circumference of the bead so that the bead is pressed in place. One of ordinary skill in the art will appreciate that other bead attachment methods may be employed in production of a dipstick useful in practicing the present invention.

The dipstick used in the methods and kits of the present invention can contain more than one bead. Preferably, the dipstick will contain from about two to about ten beads, each within its own perforation. More preferably, the plurality of bead-containing perforations will be situated in a row along one edge of the dipstick. Such a dipstick can function as an indicator card. Specifically, multiple beads with covalently attached oligonucleotide capture probes with different sequences or specificities are closely aligned on a multi-site dipstick, thereby facilitating the detection of a multiplicity of microorganisms in a single, complex biological sample. A particular bead may contain oligonucleotides representing a plurality of nonidentical nucleic acid sequences (for example, sequences from a group of related organisms) or, alternatively, a bead may only contain a plurality of identical oligonucleotides having a specific nucleic acid sequence.

Preferably, a dipstick useful in the practice of the present invention will include a bead specific for the microorganism (s) being detected, a positive control and a negative control. For example, the dipstick may include beads specific for a prokaryotic microorganism (e.g., *Gardnerella vaginalis* and/ or *Trichomonas vaginalis*) and a bead specific for a eukaryotic microorganism (e.g., *Candida albicans*) in addition to a positive control and a negative control. Such a dipstick will indicate whether the sample cell number is greater than or equal to the critical cell number for those microorganisms being detected, and will provide a more comprehensive diagnostic tool, since vaginitis may also be detected (and causative organisms distinguished) through the practice of this embodiment of the present invention.

Moreover, the dipsticks of the present invention, may include beads specific for *Neisseria gonorrhoea*, Chlamydia species, Mobiluncus species, Prevotella species. *Ureaplasma urealyticum, Prevotella bivia*, Group B Streptococci, Mycoplasma species and/or Enterobacteriaceae, in addition to a positive control and a negative control. Such a dipstick will indicate whether the sample cell number(s) is equal to or exceeds the critical cell number determined for an individual organism associated with cervicitis (e.g., *G. vaginalis*) or potentially pathogenic vaginal infection. Such dipsticks may be packaged with one or more lysis reagents capable of freeing target nucleic acid sequences for hybridization with the capture and signal probe components of the kits of the present invention. Exemplary dipsticks of this embodiment of the present invention include the following: *G. vaginalis, T. vaginalis*, Group B Streptococci and *Prevotella bivia* for prenatal risk assessment; *G. vaginalis, Mycoplasma hominis* and Mobiluncus species for bacterial vaginosis; *Chlamydia trachomatis* and *Neisseria gonorrhea* for sexually transmitted diseases; and the like.

The development of a dipstick-based assay capable of detecting the presence of multiple target nucleic acids requires identification of three key parameters: (1) the lysis or release of target nucleic acid from the sample; (2) the capture and detection of the target nucleic acid; and (3) the reagent components of the assay format. If the reagent components remain constant (i.e., hybridization conditions, wash solutions, detection enzyme, substrate and the like), one skilled in the art can design specific capture and signal oligonucleotides for hybridization with the target nucleic acid. When the conditions for capture and detection of the target nucleic acid are defined, one skilled in the art can determine lysis conditions that allow the release of the target nucleic acid from a biological sample. The optimal lysis conditions may vary slightly for each of the target microorganisms, but a balance of lytic conditions allows the simultaneous detection of the target organisms. (See, e.g., the previous discussion pertaining to the lysis method.) If these parameters are identified, the critical cell number for each microorganism can be determined in biological samples. The critical cell number may vary with the method used to acquire the sample, and can be defined as the cell number that leads to symptomatic presentation of a disorder. Symptomatic presentation is particularly relevant for disorders where an asymptomatic presence of the microorganism is possible.

It will be obvious to one of ordinary skill in the art that, although the above discussion was set forth primarily in terms of nucleic acid hybridization assays, many other uses for these dipsticks are contemplated. Any member of a ligand pair can be attached to beads in the dipstick, and the dipstick can then be used to identify the corresponding ligand member. For example, antigens or antibodies can be attached to beads, as described above, in a dipstick, and then corresponding antibodies or antigens, respectively, could be identified. In a similar manner, other ligand systems, such as biotin and streptavidin, can be used.

In a further embodiment of the claimed invention, oligonucleotide-coated beads may be employed in a microtiter well format. This format may be advantageously used when a large number of patient samples are assayed. Further, the microtiter well format is compatible with signal probes that are detected through means of a soluble reaction product.

The target nucleic acid, i.e., the nucleic acid of the microorganism of interest or an amplicon thereof, is usually a polynucleotide with an average length ranging from about 20 to about 20,000 bases or nucleotides in length. The capture probe will be substantially complementary to the target nucleic acid. A capture probe will be substantially complementary to the target nucleic acid is a polynucleotide or oligonucleotide containing naturally occurring nucleotides or their analogs (e.g., 7-deazaguanosine or inosine) sufficiently complementary to hybridize with the target nucleic acid such that stable and specific binding occurs between the target nucleic acid and the complementary capture probe. Therefore, the complementary nucleic acid sequence need not reflect the exact sequence of the target nucleic acid. For example, a non-complementary nucleotide fragment may be attached to a complementary nucleotide fragment or, alternatively, non-complementary bases or longer sequences can be interspersed into the complementary nucleic acid sequence, provided that the complementary nucleic acid sequence has sufficient complementarity with the sequence of the target nucleic acid to hybridize therewith forming a hybridization complex, i.e., duplex, and further is capable of immobilizing the target nucleic acid to a solid support.

As such, the degree of complementarity (homology) required for detectable binding (i.e., duplex formation) with the target nucleic acid will vary in accordance with the stringency of the hybridization medium and/or wash solution. The degree of complementarity will optimally be 100 percent; however, minor mismatches can be accommodated by reducing the stringency of the hybridization and/or wash solution. It will be understood by those of skill that by varying the temperature, salt concentration, etc., stable hybrids can be formed even in the presence of mismatches. Thus, despite the lack of 100 percent complementarity, functional probes having minor base differences from their target nucleic acid sequences are possible under reduced conditions of stringency. Under hybridization conditions of reduced stringency, therefore, it may be possible to modify up to 60% of a given oligonucleotide probe while maintaining an acceptable degree of specificity. However, the degree of acceptable mismatching is dependent upon the specificity required, in a manner recognized by a practitioner in the art. In addition, analogs of nucleosides may be substituted within the probe for naturally occurring nucleosides. This invention is intended to embrace these species when referring to oligonucleotide probes.

Once the target nucleic acid has undergone hybridization with the capture oligonucleotide probe to form a nucleic acid-capture probe hybridization complex, a second hybridization with a signal oligonucleotide probe must occur in order to detect the presence or absence of the hybridization complex. Signal oligonucleotide probes useful in accordance with the methods of the present invention are oligonucleotides conjugated to or conjugable with detectable labels. Various labels can be used in hybridization assays of this invention. Such labels act as reporter groups for detecting duplex, i.e., complex, formation between the target nucleic acid and its complementary signal sequence. A "reporter group" as used herein is a group having a physical or chemical characteristic that can be measured or detected. Detectability may be provided by such characteristics as enzymatic activity, color change, luminescence, fluorescence, or radioactivity, or it may be provided by the ability of the reporter group to serve as a ligand recognition site. Any haptenic or antigenic compound can be used in combination with a suitably labelled antibody for this purpose.

Exemplary enzymes of interest as reporter groups are hydrolases and, in particular, phosphatases, esterases, ureases, and glycosidases, oxidoreductases, particularly peroxidases, and the like. Fluorescent compounds include fluorescent and its derivatives, rhodamine and its derivatives, dansyl, umbelliferone, and the like. Chemiluminescers include luciferin, luminol, oxetane-diones, and the like. The above list is illustrative only, and the choice of label depends on sensitivity requirements, ease of conjugation with the probe, stability requirements, and available instrumentation.

The extent of hybridization may be quantified using a method or technique of fluorescent quenching, described in copending U.S. patent application Ser. No. 558,967. Dipstick (i.e., insoluble) diagnostic format fluorescent quenching employs a solid support, such as nylon, that fluoresces when irradiated with ultraviolet light (240 to 400 nanometers (nm)). Colorimetric insoluble enzymatic product deposited on the solid support during the preferred assay procedure quenches the fluorescence of the solid support, thereby providing a means of quantifying the amount of product using commercially available fluorometers. The solid supports described herein do not require a plurality of fluorescent chromophoric groups to be bound thereto, but rather rely on the intrinsic or natural fluorescence of the polymeric material forming the solid support. The irradiation and detection of fluorescence in a hybridization assay methodology utilizing this type of support are also not dependent on the use of narrow or specific wavelengths of ultraviolet or visible light.

For example, a sandwich may be formed in which a target nucleic acid is hybridized to the solid support; a signal biotinylated-oligonucleotide is then hybridized to the target nucleic acid; and reporter enzyme conjugated to streptavidin is bound to the biotinylated oligonucleotide. After sandwich formation, reporter enzyme product is allowed to deposit or accumulate on the surface of the solid support. In most cases, the quantity of enzymatic product produced is directly proportional to the quantity of captured target nucleic acid. The solid support is then irradiated with an ultraviolet light source (240 to 400 nm) and the resultant fluorescence is determined with a fluorometer. The intensity of the measured fluorescence is inversely proportional to the quantity of enzymatic product deposited on the solid support. Alternatively, if the reporter enzyme product is colored, product deposited or accumulated on the surface of the bead can be qualitatively and/or quantitatively determined. Quantitative determinations may be performed visually or by an instrument capable of analyzing and/or measuring gradations of color, either directly or using shades of grey. Such quantitative determinations generally include a comparison to standards.

If the fluorescence quenching method is used, the only required property of an enzymatic product useful in quantifying the amount of captured target nucleic acid is the ability to quench or mask the fluorescence of the solid support. Any type of enzyme which produces a colorimetric product can be utilize in the fluorescent quenching assay. Exemplary enzymes include horseradish peroxidase (HRP), alkaline phosphatase (AP), beta-galactosidase and the like. Representative substrates for each exemplary enzyme include 4-methoxynaphthol (4MN), 5-bromo-4-chloroindoyl-3-phosphate/nitroBlue tetrazolium (NBT), and o-nitrophenyl-beta-D-galactopyranoside (ONG), respectively.

Since the quantity of enzymatic product produced is proportional to the quantity of captured target nucleic acid, and the quenching of fluorescence by the colored product is proportional to the quantity of product produced, a quantitative determination of captured target nucleic acid can be made. In most cases, the relation between captured target nucleic acid and fluorescence quenching is linear.

In this embodiment, the solid support must necessarily possess some type of fluorescence when irradiated by ultraviolet or visible light. The fluorescence can be intrinsic or inherent to the material composing the solid support, or fluorescent compounds can be bound (either covalently or non-covalently) to the solid support during the manufacturing or derivitization process. Exemplary fluorescent compounds include fluorescent, Texas Red, rhodamine and the like.

Dipstick format diagnostics of the present invention may be evaluated by visual assessment only. In this embodiment, the bead will turn from its natural color to an indicator color, such as blue, to indicate positive results. For example, a dipstick might be designed to turn an indicator color visible to the eye when a sufficient amount of a target nucleic acid is present. This embodiment of the present invention will not require irradiation of the sample with ultraviolet light or detection with a fluorometer.

Alternatively, direct determination or quantitation of fluorescent enzymatic product may be employed in a soluble detection format (e.g., 96 well format) of the present invention. To obtain accurate results, however, the fluorescent enzymatic product must be measured in an environment that neither quenches the product nor is fluorescent itself. Since the preferred solid supports described herein possess a very high intrinsic fluorescence in their native state, it is not possible to accurately measure a fluorescent soluble enzymatic product in the presence of the preferred solid support. Such a solid support must therefore be removed from the substrate solution or the solution decanted and placed in a separate vessel to allow accurate determination of fluorescence.

Alternatively, for fluorescent signal detection, colored or coated polymeric beads may be employed. Coloring the preferred solid support with a dye of any color significantly reduces or quenches the intrinsic fluorescence thereof. Coating serves to mask any intrinsic fluorescence of a particular solid support. This reduction in fluorescence permits the solid support to be present during soluble enzymatic product fluorescence measurement, thereby obviating the need to transfer solutions or solid supports. Fluorescent signal detection may also be accomplished by employing microtiter wells directly coupled to the capture nucleic acid sequence.

If a bead or solid support (preferably dyed or colored) remains present during fluorescent signal detection, bead-to-bead or solid support-to-solid support fluorescence must be relatively uniform. The standard deviation of bead-to-bead intrinsic fluorescence should not exceed the standard deviation of the assay (typically 1 to 10%) or of the detected fluorescence (typically 1 to 5%), in order to fully utilize the potential of the fluorescent substrate. This procedure is used in the microtiter well format of the present invention, where a soluble fluorescent product is measured directly in the presence of the colored bead. Less meaningful measurements are obtained when deviations greater than those set forth above occur.

Virtually any color of dichlorotriazine, azo, or other permanent dyes will reduce the intrinsic fluorescence of the nylon approximately 500-fold. Exemplary dye colors are black, blue, red, green, yellow, purple, orange and the like, with the only requirement with respect to dye color being that the dye not fluoresce at the same wavelength as the fluorescent enzymatic product.

In addition to quenching the natural fluorescence of the preferred solid support, coloring the supports allows the development of solid supports with different capture oligonucleotides or different target nucleic acid specificities that are distinguishable by color. The ability to distinguish different solid supports by color has the following advantages: 1) quality control can be enhanced, because solid supports possessing different specificities can be identified and distinguished; and 2) contrast between a colorimetric enzymatic product and the surface of the solid support can be maximized. This allows a greater level of sensitivity to be achieved when assay results are determined by visual inspection.

In another aspect of the present invention, a method and kit are provided for selectively detecting a Group I microorganism selected from the group consisting of gram positive bacteria and fungi, and at least one other Group II microorganism selected from the group consisting of protozoa, mycoplasmas and gram negative bacteria in a single, complex biological sample, the method comprising: (a) lysing the cells of a Group I and a Group II microorganisms by combining the sample with a lysis solution, thereby releasing nucleic acid from the microorganisms; (b) contacting the nucleic acid released from the microorganisms, under hybridizing conditions, with an oligonucleotide capture probe that selectively hybridizes to the nucleic acid of the Group I microorganism and an oligonucleotide capture probe that selectively hybridizes to the nucleic acid of the Group II microorganism to form a Group I microorganism-capture probe hybridization complex and a Group II microorganism-capture probe hybridization complex, respectively; and (c) detecting the hybridization complexes as an indication of the presence of the Group I microorganism and the Group II microorganism in the sample.

In this method of the present invention, the Group I microorganism includes gram positive bacteria and fungi (e.g., yeast), whereas the Group II microorganism includes, but is not limited to, protozoa, mycoplasmas and gram negative bacteria. In a presently preferred embodiment, the Group I microorganism includes, but is not limited to, the following microorganisms: Group B Streptococci and *Candida albicans*; the Group II microorganism includes, but is not limited to, the following microorganisms: *Gardnerella vaginalis* and *Trichomonas vaginalis*. Additionally, *Prevotella bivia*, *Ureaplasma urealyticum*, Mobiluncus species, Mycoplasma species, *Neisseria gonorrhea*, Enterobacteriaceae and Chlamydia species can also be selectively detected.

As with the previously described method, the discussion pertaining to the method for releasing intact nucleic acid from a microorganism is fully applicable to the method at hand. As such the cells of the various microorganisms are lysed by combining the complex biological sample containing the microorganisms with a lysis solution comprising a low ionic strength buffer and a detergent, the lysis solution having a pH ranging from about 7.0 to about 12.0; and heating the combined solution to above about 65° C. for more than about five minutes to release the nucleic acid from the microorganisms, wherein the lysis solution is capable of releasing intact nucleic acid from the microorganism in the absence of mechanical force.

Once released from the cells of the microorganisms of interest, the specific nucleic acid sequences of interest, i.e., the target nucleic acid sequences or an amplicon thereof, are detected and identified through the use of nucleic acid hybridization assays. As such, the previous discussion pertaining to the use of nucleic acid hybridization assays and, in particular, sandwich assays to detect a microorganism of interest is fully applicable to this detection method.

In a further aspect of the present invention, a diagnostic method is provided for determining whether a patient is afflicted with bacterial vaginosis (BV), the method comprising: (a) determining the pH of a vaginal sample obtained from the patient; (b) detecting the *Gardnerella vaginalis* (Gv) cell level in the vaginal sample in a time period of about 6 hours or less; and (c) determining that the patient is BV-positive if the pH value of the vaginal sample is greater than about 4.5 and the Gv cell level of the vaginal sample is greater than or equal to a critical Gv cell number.

In almost every instance, the vaginal pH in women with BV is higher pH 4.5, whereas the vaginal pH of women who are clinically negative for BV is almost always less than 4.5. However, pH alone is not diagnostic for BV, because other conditions can lead to elevated vaginal pH. While women with BV have elevated levels of *G. vaginalis* in their vaginal tract, enumeration of *G. vaginalis*, taken alone, is not a good indicator of BV, because BV-negative women frequently have elevated levels of *G. vaginalis* in their vaginas. The above method permits rapid measurement of pH and *G. vaginalis* levels in a patient sample, as an indication of Bacterial Vaginosis.

This method makes use of the finding that a pH>4.5 in combination with an elevated, i.e., clinically significant, level of *G. vaginalis* in a vaginal sample are diagnostic for BV, even though each parameter taken alone is not diagnostic. This diagnostic method for determining whether a patient is afflicted with bacterial vaginosis involves determining whether the *G. vaginalis* cell number in a patient sample is greater than or equal to a critical *G. vaginalis* cell number. The critical *G. vaginalis* cell number is a predetermined cell number that is associated with BV. The critical *G. vaginalis* cell number may vary with the sample collection method employed, and is defined herein to be either cell number or cell concentration. To initially identify the critical *G. vaginalis* cell number corresponding to a particular sampling method and assay procedure, the sampling method will be used to obtain specimens from a sufficient number of women that have been clinically diagnosed as BV-positive or BV-negative to establish the critical *G. vaginalis* cell number. A range of *G. vaginalis* cell numbers from the BV-positive women will be determined, and the critical *G. vaginalis* cell number will represent the bottom of this range. This critical number is tied to the selected sampling method. Determination of the critical *G. vaginalis* cell number will be dependent upon the sample collection procedure, such as vaginal wash, vaginal swab, or other sample obtaining means, as well as the assay used to measure the number of *G. vaginalis* cells present in that sample within a period of 6 hours or less. The *G. vaginalis* cell number may be measured by nucleic acid hybridization techniques, by techniques involving antibody-antigen interactions, or by any other method whose results can be correlated with a *G. vaginalis* cell number or *G. vaginalis* cell concentration. While the critical *G. vaginalis* cell number may be dependent on the methods chosen for sample collection and for *G. vaginalis* enumeration, the critical *G. vaginalis* cell number will be consistent over a 10-fold range for any selected protocol.

Using the selected sampling method and assay procedure, the *G. vaginalis* cell number of the sample will be established by comparing patient test results to a standard curve generated by concurrently evaluating standards derived from a known number of purified, cultured *G. vaginalis*. Serial dilutions of quantitated, cultured *G. vaginalis* are subjected to the same assay procedures as the patient samples. The signal intensity of each patient sample is compared to signal intensities of the diluted standards, and the patient sample can be correlated with an amount of *G. vaginalis* equivalent to that in the matching standard dilution.

Alternatively, a specific molecule that serves as the target of the *G. vaginalis* assay can be purified from a known number of cultured *G. vaginalis* and used as a standard for comparison to the patient sample results. For example, if 16S rRNA is the target of the assay, purified 16S rRNA can serve as the standard, with a given amount of 16S rRNA corresponding to a known number of *G. vaginalis* cells. In this instance, the patient sample results could be expressed in units equivalent to molecules of 16S rRNA; BV-positive and BV-negative women are characterized according to how many 16S rRNA equivalents are present in the sample. This approach could be used for any other purified molecule obtained from a known number of *G. vaginalis* cells. If desired, a separate experiment could determine the number of 16S rRNA molecules per *G. vaginalis* cell, and thereafter the 16S rRNA standard could be used, but the results could be expressed per *G. vaginalis* cell number. Since the number of target molecules (such as 16S rRNA) per cell can vary during different stages in the *G. vaginalis* cell growth cycle, the number of correlate molecules per cell should be established using a known number of *G. vaginalis* cells that are in the mid-log phase of growth. For consistency, this numerical equivalency will be determined only once, and thereafter the purified target molecule, such as 16S rRNA, can be used as a standard, with conversion to numbers of *G. vaginalis* cells according to the established numerical equivalency.

Once the selected method has been used to determine the number of *G. vaginalis* cells per sample from the BV-positive and the BV-negative groups, the critical *G. vaginalis* cell number may be determined (i.e., the minimum number of *G. vaginalis* cells associated with BV-positive women). While some of the BV-negative women may have *G. vaginalis* cell numbers greater than the critical level, these women will nearly always be found to have a vaginal pH<4.5, and thus will be diagnosed as BV-negative when the diagnostic kit instructions are followed.

Within the present invention, a critical cell number may be determined for an organism other than *G. vaginalis* in a manner similar to that set forth above for determining critical *G. vaginalis* cell number. For instance, the critical cell number for women presenting with Candidiasis may be determined relative to indigenous Candida species levels found in the vagina. For organisms not normally found in vaginal fluid, no critical cell number exists. The presence of such cells in any number indicates an abnormality. For example, the lower detection limit of the kit for *T. vaginalis* under ideal conditions is about $5 \times 10^3$ cells. This cell number or one as close to it as possible will be used to indicate positive results of a *T. vaginalis* probe.

The concentrations of the reaction components of a solid phase assay kit of the present invention will be adjusted to ensure that a positive signal will be obtained only if the amount of *G. vaginalis* present is equal to or greater than the critical *G. vaginalis* cell number. Under ideal conditions, the lower limit of detection of the kit for *G. vaginalis* is about $2 \times 10^5$ cells. The critical *G. vaginalis* cell number will generally range from about $5 \times 10^6$ to about $5 \times 10^9$ cells per mL of vaginal fluid, with about $8 \times 10^6$ to about $10^9$ cell/mL of vaginal fluid preferred, and about $2 \times 10^7$ cells/mL of vaginal fluid particularly preferred. For the purposes of this description, "about $2 \times 10^7$ cells/mL of vaginal fluid" means a *G. vaginalis* cell level within the range from about $5 \times 10^6$ cells/mL to about $5 \times 10^9$ cells/ml.

Vaginal fluid samples that may be tested in accordance with the present invention may be obtained in any conventional manner. Exemplary sample obtaining methodologies involve the use of a vaginal swab, vaginal wash techniques or the like.

The pH determining step of the methods of the invention may be accomplished by conventional techniques, such as by contacting a sample (e.g., a vaginal swab or speculum) with pH paper or another pH indicating substrate and observing an alteration in the color of the paper or substrate that is indicative of relevant sample pH. The pH indicator may be included within a diagnostic kit of the present invention as a separate structural unit or as a portion of the structure of a diagnostic indicator card or dipstick. Alternatively, the pH indicator might be provided by the clinician. In addition, pH may be measured with electrodes or with commercially available pH indicators; alternatively, known pH indicators can be immobilized on a solid support.

Similarly, the *G. vaginalis* cell level may be determined by any method yielding an accurate measurement thereof that may be performed in 6 hours or less. Consequently, probes, including oligonucleotide sequences that are complementary to *G. vaginalis* DNA or RNA, antibodies selective for *G. vaginalis* or the like, may be used for this purpose. Direct hybridization assay techniques may be used in making the *G. vaginalis* cell level determination. Sandwich assay techniques employing oligonucleotide capture probes or antibodies are presently preferred methods for determining the *G. vaginalis* cell level determination. Of these, the sandwich assay technique employing oligonucleotide capture probes is the presently preferred method. As such, the previously discussion pertaining to both the lysis method and the nucleic acid hybridization methods is fully applicable to the diagnostic method for determining whether a person is afflicted with bacterial vaginosis.

In a preferred embodiment of this method, target nucleic acid is typically sequestered (captured) from the original patient sample by hybridization (i.e., pairing of complementary bases) with oligonucleotide capture probes that are covalently immobilized on the surface of a solid support. Alternatively, the target nucleic acid from the original patient sample may be amplified to form an amplicon which is captured and hybridized to the signal probe. The captured target nucleic acid is then hybridized to a signal oligonucleotide probe having a detectable label bound thereto, or having the capability of binding to a moiety having a detectable label bound thereto. The signal probe is specific for an alternative site on the target nucleic acid. Alternatively, signal hybridization can be performed simultaneously with capture hybridization by including the signal probe within, for example, the hybridization solution. This results in a "sandwich" of the capture oligonucleotide probe:target nucleic acid:signal oligonucleotide probe. The solid support is washed to remove unhybridized material, and the labelled nucleic acid is then measured in accordance with detectable characteristics of the label.

Alternatively, in sandwich assays involving antigen/antibody technology, antigen is either present in the original sample, extracted therefrom or released from organisms contained in the original sample by reagents that disrupt the cell wall and/or membrane. The antigen is sequestered (captured) from the test sample by interaction with antigen specific antibody that is covalently immobilized on the surface of a solid support. The captured target antigen may then be incubated with a signal antibody having a detectable label bound thereto, or having the capability of binding to a moiety having a detectable label bound thereto. The signal antibody is specific for an alternative site on the target antigen. Alternatively, signal antibody binding can be performed simultaneously with capture by including the signal antibody within, for example, the incubation solution. This results in a "sandwich" of the capture antibody:target antigen:signal antibody. The solid support is washed to remove unbound signal antibody, and the labelled antigen is then measured in accordance with detectable characteristics of the label.

In the sandwich assays described above, biotin/avidin or biotin/streptavidin technology may also be employed. Specifically, the biotin/avidin interaction may be exploited to couple a more generalized detection system to the oligonucleotide probe or antigen/antibody sandwich assays. For example, the signal probe of the sandwich assay may be covalently bound to biotin. This biotin-labelled signal probe can then be incubated with avidin or streptavidin, its complementary ligand, having a detectable label bound thereto. This results in the detection of a "sandwich" of the capture oligonucleotide probe:target nucleic acid: signal oligonucleotide probe/biotin:avidin/detectable label. In this embodiment, avidin/detectable label can be prepared in large scale and can bind to signal/biotin moieties in a variety of sandwich assays. Other ligand pairs are also useful in the solid phase assays of the present invention. Exemplary of such additional ligand pairs are lectin:sugar, hormone:hormone receptor and the like.

The diagnostic method of the present invention correlate well with traditional clinical diagnoses of BV. Illustrative patient samples used for comparative diagnostic testing were obtained from single, white females in their 20's at the Student Health Clinic at the University of Washington. The "normal" (i.e., BV-negative) patients were attending the clinic for routine examinations and showed no symptoms of vaginitis. pH was routinely measured at the time the samples were taken.

In these studies, a vaginal sample was obtained and analyzed in accordance with conventional techniques to obtain a conventional BV diagnosis. Subsequently, a vaginal wash was obtained, and a portion of this sample was mixed with concentrated 5M GuSCN solution to yield a final concentration of 3M GuSCN. The sample was concentrated onto nitrocellulose paper by slot blot techniques and then hybridized with a radiolabelled, *G. vaginalis*-oligonucleotide probe (i.e., the probe hybridizes selectively with 16S rRNA of *G. vaginalis* when challenged with more than 70 other potentially cross-reacting species that may be found in the normal microflora of the vagina). Hybridization of $^{32}$P-labelled probe to each sample was determined by autoradiography, and levels of probe hybridization to samples and standards were compared.

A comparison of patient sample slot blot results with standards of known target nucleic acid concentrations allowed quantitative determination of the number of *G. vaginalis* cells in the patient samples. When the pH (greater than 4.5) and number of *G. vaginalis* cells (greater than or equal to approximately $2\times10^7$) diagnostic criteria of the present invention were used in evaluating the slot blots, BV was detected with a sensitivity of 95.3% and a specificity of 98.6.%. These diagnostic comparative results are set forth in Example 6 below.

The present invention also contemplates diagnostic kits for determining whether a patient is afflicted with BV, the kit comprising: (a) a first indicator capable of indicating a pH greater than about 4.5; and (b) a second indicator capable of indicating a Gv cell level greater than or equal to a critical Gv cell number or level associated with the disease state. In a presently preferred embodiment, the second indicator comprises an oligonucleotide capture probe that selectively hybridizes to the nucleic acid of *Gardnerella vaginalis* (Gv) to form a *Gardnerella vaginalis* nucleic acid-capture probe hybridization complex, the oligonucleotide capture probe is immobilized on a solid support. In this instance, the *Gardnerella vaginalis* nucleic acid-capture probe hybridization complex is detected by a signal oligonucleotide probe which is not complementary to the capture probe and which hybridizes to the nucleic acid of *Gardnerella vaginalis*. It will be understood by those of skill that the second indicator can be in the form of a diagnostic dipstick.

With respect to the first indicator, the kit may contain a strip of pH indicating paper and a diagnostic indicator card, such as a dipstick. A cell disruption buffer/hybridization solution or a ligand incubation solution (optionally containing appropriate signal moieties) may also be included within the kits of the present invention to facilitate employment of sandwich assay techniques. Alternatively, the pH indicator, i.e., the first indicator, may be structurally integrated with the *G. vaginalis* cell number indicator, i.e., the second indicator. The kits may be used in manual or semi-automatic testing procedures, and are preferably employable in sandwich assay techniques.

Moreover, indicators of the presence of other organisms, such as Candida spp. (e.g., *C. albicans, C. glabrata, C. kefyr, C. krusei, C. parapsilosis* and *C. tropicalis*), *Trichomonas vaginalis, Neisseria gonorrhoea*, Chlamydia spp., Mobiluncus spp., Prevotella spp., Mycoplasma spp., *Ureaplasma urealyticum, Prevotella bivia*, Enterobacteriaceae, Group B Streptococci or the like, may also be included in the kits of the present invention. In this manner, the kits of the present invention may be employed to detect BV, vaginitis or cervicitis.

The diagnostic kits of the present invention can be used as part of a semi-automated method for diagnosis of, for example, bacterial vaginosis. Such kits would provide for the detection of *G. vaginalis* when present at or above the level characteristic of BV, and may include a sample obtaining means, such as a vaginal swab; a pH indicating means, such as pH paper; lysis buffer/hybridization solution and ligand incubation solution; and *G. vaginalis* cell number indicating means, such as a diagnostic dipstick. This kit may be used in conjunction with an incubation apparatus (such as a heating block), an automated assay device and/or a bead reader.

A practitioner using the semi-automated method of the present invention for the diagnosis of BV will follow a procedure substantially as described below:

1) Obtain a vaginal swab and apply the swab to provided pH paper;
2) Insert the swab into a tube containing a lysis solution comprising a low ionic strength buffer and a detergent, the lysis solution having a pH ranging from about 7.0 to about 12.0;
3) Squeeze out the swab, place the tube into a well of a heating block, at heat to a temperature above about 65° C. for approximately five minutes to release the nucleic acid from the microorganism in the absence of mechanical force;

4) Add 5M GuSCN solution to a final concentration of 3M.
5) Transfer the solution to the first sample well in an automated dipstick processor, which automatically completes the assay development in approximately 30 minutes.
6) Visually determine whether a colored substance has been deposited on the bead.

In this semi-automated methodology, step 1 corresponds to determining pH of a vaginal sample obtained from the patient. Step 2 generally involves the use of a lysis solution comprising a low ionic strength buffer and a detergent, the lysis solution having a pH ranging from about 7.0 to about 12. Steps 2–6 constitute determining whether the critical *G. vaginalis* cell number is equalled or exceeded by the patient sample.

These methods and kits are advantageous in that they provide accurate BV diagnosis rapidly and reproducibly, without a requirement for highly skilled, labor-intensive analysis. The methods of the present invention may be accomplished in 6 hours or less, and preferably are accomplished in 1 hour or less.

Also, the methods and kits of the present invention eliminate the need for skill in identifying clue cells or evaluating wet mounts. Consequently, the methods of the present invention could be practiced and the kits of the present invention could be used by individuals without the aforementioned skills. Specifically, a laboratory technician or physician's assistant could employ the methods and kits of the present invention with virtually no special training. Another ramification of using the methods and kits of the present invention is that the subjectivity involved in wet mount and Gram stain analysis is replaced with more objective procedures. Specifically, analyst-to-analyst variation is eliminated through the use of the present invention.

In the physician's office setting, physical examinations and wet mounts are primarily relied upon to diagnose BV. These methodologies are less accurate than the gold standard method, but the gold standard method is generally considered too complicated to perform in an office environment. The methods and kits of the present invention can be utilized in the office setting to achieve diagnostic results comparable to those provided by the gold standard method or the physical examination/wet mount method.

In an alternative embodiment, patient samples may be collected, processed and analyzed to selectively detect the presence of *Gardnerella vaginalis*, Candida species (e.g., *C. albicans, C. glabrata, C. kefyr, C. krusei, C. parapsilosis* and *C. tropicalis*), and/or *Trichomonas vaginalis*. Samples are collected from symptomatic females presenting with vaginal complaint who have not been treated with anti-bacterial or anti-fungal medication within the week prior to sample collection and who have not douched within 24 hours.

In a preferred procedure, a sterile swab is used to obtain vaginal fluid samples. Dacron swabs with pre-scored handles are particularly preferred for sample collection. Samples are obtained by twisting or rolling the swab against the vaginal wall two or three times, ensuring that the entire circumference of the swab has touched the vaginal wall. The swab is then placed in a sample collection tube, the pre-scored handle of the swab is broken, and the tube is capped. The unlubricated speculum is removed from the patient, and the vaginal pH is determined by touching a pH indicator strip to the speculum.

In a protocol for immediate sample preparation, the swab/sample is transported immediately at room temperature for processing and analysis. If the swab/sample cannot be immediately processed, the swab/sample is held at 0° C. to 8° C. for four hours or at room temperature for one hour.

For processing, lysis solution is added to the swab/sample, which is then swirled or agitated in the lysis solution for about 10–15 seconds. The tube containing the swab and lysis solution is heated at 85° C. for 5 minutes, and hybridization solution is mixed with the sample. At this point, samples may be stored for up to 24 hours at room temperature.

The swab contents are expressed by twirling the swab against the side of the tube, and the solution remaining in the tube may then be processed on an automated instrument. Generally, the solution remaining in the tube is filtered prior to further processing. In a preferred embodiment, the sample is placed in the first well of a reagent cassette or multi-cavity container, and the semi-automated instrument moves a dipstick through each well of the cassette, thereby processing the sample. A preferred dipstick contains five beads—a procedural control, a negative control, a bead with *Gardnerella vaginalis*-specific capture probe, a bead with Candida species-specific capture probe, and/or a bead with *Trichomonas vaginalis*-specific capture probe. It is preferred that the detection of these three organisms be achieved through a colorimetric signal system, wherein the presence of color on a test bead at the end of automated sample processing is indicative of a detectable level of nucleic acid from that target organism. The intensity of color on a bead can be estimated either visually or by a measuring device, such as an image analyzer or reflectometer. The procedural control ensures that the procedure has been correctly performed and serves as a reagent quality check. The negative control evaluates non-specific binding to the beads.

The invention will be described in greater detail by way of specific examples. The following examples are offered for illustrative purposes, and are intended neither to limit or define the invention in any manner.

EXAMPLE

In the example section below, Example 1 describes quantitation of horseradish peroxidase insoluble product on $\frac{3}{32}$nd inch nylon beads using the fluorescence quenching technique. Example 2 describes the quantitation of alkaline phosphatase insoluble product on $\frac{3}{32}$nd inch nylon beads using the fluorescence quenching technique. Example 3 describes a comparison of direct fluorescence using soluble 4-methyl-umbelliferone in the presence of black and natural colored nylon beads. Example 4 describes the reduction in fluorescence of nylons beads by dying the beads with a multiplicity of different colors. Example 5 illustrates the various lysis methods which can be used to release nucleic acid from the target microorganism. Example 6 illustrates the correlation between the diagnostic criteria employed in the practice of the present invention and conventional BV diagnostic techniques. Example 7 describes methods and kits for simultaneous detection of *Gardnerella vaginalis*, Candida species, and *Trichomonas vaginalis* target nucleic acid in a complex biological sample. Example 8 describes improved methods and kits for simultaneous detection of *Gardnerella vaginalis*, Candida species and *Trichomonas vaginalis* target nucleic acids in a complex biological sample. Finally, Example 9 describes a preferred method for simultaneous detection of *Gardnerella vaginalis*, *Trichomonas vaginalis*, and Group B Streptococci in a complex biological sample, and in particular, from a vaginal sample.

MATERIALS

Solutions

APB buffer is 0.18M NaCl, 0.05M Tris-HCl, pH 7.6, 5 mM EDTA, and 0.5% (v/v) Tween® 20.

TMNZ buffer is 0.05M Tris, pH 9.5, 1 mM MgCl$_2$, and 0.5 mM ZnCl$_2$

FW (filter wash) is 0.09M sodium chloride, 50 mM Tris, pH 7.6, and 25 mM EDTA.

SDS/FW is FW and 0.1% (w/v) sodium dodecyl sulfate (SDS).

HRP (horseradish peroxidase) substrate solution is 0.1M sodium citrate, pH 6.5, 0.2M sodium phosphate, 0.5 mg/mL 4-methoxy-1-naphthol, 0.02 mg/mL 3-methyl-2-benzothiazolinone hydrazone and 0.0135% (v/v) hydrogen peroxide.

AP (alkaline phosphatase) substrate solution is 1 mM 5-bromo-4-chloroindoyl-3-phosphate, 1 mM nitroBlue tetrazolium, and 0.01% (v/v) Tween® 20 in TMNZ.

5M GuSCN is 5M guanidinium thiocyanate, 83.5 mM Tris, pH 8.0, 8.35% formamide, and 16.7 Mm EDTA.

3M GuSCN is 3M guanidinium thiocyanate, 50 mM Tris, pH 8.0, 5% formamide, and 10 mM EDTA.

Proteinase K lysis solution is 1 mg/mL proteinase K, 0.5% (w/v) SDS, and 5% N-lauroylsarcosine (sarcosyl).

Lysis and hybridization solution is 3M guanidinium thiocyanate (GuSCN), 50 mM Tris, pH 7.6, 2% sarcosyl, and 25 mM EDTA.

Hybridization/slot blot solution is 90 mM Tris, pH 8.0, 0.6M NaCl, 10 mM EDTA, 0.5% SDS, 5× Denhardt's (1× Denhardt's =0.02% (w/v) Ficoll, 0.02% (w/v) polyvinylpyrrolidone, and 0.02% (w/v) bovine serum albumin, Fraction V), 30% formamide, and 100 µg/mL homomix (hydrolyzed RNA yielding RNA fragments of ≈5–15 bases in length).

CAP buffer is 0.1M sodium citrate, pH 6.5 and 0.2M sodium phosphate.

The fluorescent substrate for alkaline phosphatase is 0.02 mM 4-methyl-umbelliferyl phosphate, 0.05M Tris, pH 9.5, 1 mM MgCl$_2$, and 0.5 mM ZnCl$_2$.

The sequences below are preferred probes. Preferred are those probes that hybridize to regions of the ribosomal RNA with minimal secondary and tertiary interactions, such as those listed below. The advantage of such probes is that the hybridization can be carried out without the additional step of heat denaturing the sample nucleic acid.

Oligonucleotide Sequences for *Prevotella bivia*
PB002: 5'GGA-ACA-CGT-TCC-CCA-CTT-ATC-CCC3' (SEQ ID NO:1)
PB004: 5'TGC-CCT-AGG-TCG-ATC-CTT-ACG-GTC3' (SEQ ID NO:2)
PB006: 5'GGG-ATG-CTT-AAT-GCT-TTC-GCT-TAG3' (SEQ ID NO:3)
PB008: 5'TAC-GGT-CAC-GAA-CTT-CAG-GCA-CCC3' (SEQ ID NO:4)

for *Prevotella melaninogenica*
BM003: 5'GTC-ATT-ATC-TCT-AAA-TCC-TTC-CTC3' (SEQ ID NO:5)
BM005: 5'CAA-TCA-CCA-GTT-TTG-CCC-TAG-GCC3' (SEQ ID NO:6)
BM006: 5'GAT-CCT-TGG-GGT-CAC-GGA-CTT-CAG3' (SEQ ID NO:7)

for Candida species
CAL001: 5'TTC-CTC-GTT-AAG-GTA-TM -ACA-TTG3' (SEQ ID NO:8)
CAL002: 5'CGT-TAA-GGT-ATT-TAC-ATT-GTA-CTC3' (SEQ ID NO:9)
CAL003: 5'AAG-GTA-TTT-ACA-TTG-TAC-TCA-TTC3' (SEQ ID NO:10)
CAL004: 5'TTC-CTC-GTT-AAG-GTA-TIT-ACA-TTG-TAC3' (SEQ ID NO11)
CAL015: 5'TTG-TTC-CTC-GTT-AAG-GTA-TIT-ACA-TTG-TAC-TC3' (SEQ ID NO:12)
CAL020: 5'GTC-AAT-CCT-TAT-TGT-GTC-TGG-ACC-TGG-T3' (SEQ ID NO:13)

for *Chlamydia trachomatis*
CT003: 5'ACC-GTC-TTC-TCT-TAT-TCC-CAA-GCG3' (SEQ ID NO:14)
CT005: 5'TCN-AGC-GGG-TAT-TAA-CCG-TCT-TCT3' (SEQ ID NO:15)

for Enterobacteriaceae
EC020: 5'GTC-CCC-CTC-TTT-GGT-CTT-GCG-ACG-TTA-T3' (SEQ ID NO:16)
EC021: 5'CAT-TAC-TCA-CCC-GTC-CGC-CAC-TCG-TC3' (SEQ ID NO:17)

for *Gardnerella vaginalis*
GV003: 5'AGA-CGG-CTC-CAT-CCC-AAA-AGG-GTT3' (SEQ ID NO:18)
GV006: 5'CAC-TCA-CCC-AAA-AGG-CTT-GCT-CCC3' (SEQ ID NO:19)
GV008: 5'GTC-CGA-NAC-AGA-ACC-CGT-GGA-ATG3' (SEQ ID NO:20)
GV009: 5'GGC-CCC-ACA-TCC-AGC-GTC-CAC-CGT3' (SEQ ID NO:21)
GV015: 5'TAC-ACT-CAC-CCA-AAA-GGC-TTG-CTG-CCC3' (SEQ ID NO:22)
GV017: 5'GTC-CGA-CAC-AGA-ACC-CGT-GGA-ATG3' (SEQ ID NO:23)
GV018: 5'CCC-CAC-ATC-CAG-CGT-CCA-CCG3' (SEQ ID NO:24)
GV019: 5'GGC-CCC-ACA-TCC-AGC-GTC-CA3' (SEQ ID NO:25)
GV020: 5'GGC-TTG-CTG-CCC-AAT-CAA-AAG-CGG-TTT-AC3' (SEQ ID NO:26)

for *Mycoplasma hominis*
MH001: 5'GTG-ATT-CTC-CAC-CGA-CTA-ATG-ATC3' (SEQ ID NO:27)
MH002: 5'CCG-ACA-AGG-TAC-CGT-CAG-TCT-GCA3' (SEQ ID NO:28)
MH003: 5'CAT-TTC-CTA-TTG-CAA-ATG-TTC-TTC3' (SEQ ID NO:29)
MH004: 5'CCA-TCT-GTC-ACT-CCG-ATA-ACC-TCC3' (SEQ ID NO:30)
MH005: 5'CCA-GTC-CTA-CCT-TAG-GCG-GTC-GCC3' (SEQ ID NO:31)
MH008: 5'CTG-CAA-TCA-TTT-CTT-ATT-GCA-AAT3' (SEQ ID NO:32)
MH009: 5'CTG-ACA-AGG-TAC-CGT-CAG-TCT-GCA3' (SEQ ID NO:33)

for *Mobiluncus curtesii complex*
MSP003: 5'ACC-ATC-AAC-ACA-CCC-AAA-AGC-ATG-CCT-TT3' (SEQ ID NO:34)

for *Mobiluncus mulieris*
MSP004: 5'ACC-ATC-AAC-ACA-GCC-AAA-ACT-GTG-CCT-TT3' (SEQ ID NO:35)

for *Neisseria gonorrhoeae*
NG001: 5'CTC-CGT-CTC-CGG-AGG-ATT-CCG-CAC3' (SEQ ID NO:36)
NG003: 5'ATA-TTG-GCA-ACA-GCC-TTT-TCT-TCC3' (SEQ ID NO:37)
NG004: 5'GCC-GCC-GAT-ATT-GGC-AAC-AGC-CTT3' (SEQ ID NO:38)
NG007: 5'ATA-TTG-GCA-ACG-GCC-TTT-TCT-TCC3' (SEQ ID NO:39)
NG008: 5'GCC-GCC-GAT-ATT-GGC-AAC-GGC-CTT3' (SEQ ID NO:40)
NG015: 5'TGC-TTT-CCC-TCT-CAA-GAC-GTA-TGC-G3' (SEQ ID NO:41)

for *Streptococcus agalactiae*
SA003: 5'TAC-CGT-CAC-TTG-GTA-GAT-TTT-CCA-CTC-C3' (SEQ ID NO:42)
SA005: 5'GAT-TTT-CCA-CTC-CTA-CCA-ACG-TTC-TTC-TC3' (SEQ ID NO:43)
SA006: 5'CCT-ACC-AAC-GTT-CTT-CTC-TAA-CAA-CAG-AGC3' (SEQ ID NO:44)
SA010: 5'GGT-AGA-TTT-TCC-ACT-CCT-ACC-AAC-GTT-CTT-CTC3' (SEQ ID NO:45)
SA018: 5'GGT-AGA-TTT-TCC-ACT-CCT-ACC-AAC-GTT-C3' (SEQ ID NO:46)
for *Streptococcus pyogenes*
SP001: 5'GAT-TTT-CCA-CTC-CCA-CCA-TCA-TTC-TTC-TC3' (SEQ ID NO:47)
for *Trichomonas vaginalis*
TRV012: 5'ATC-CTN-AAA-GAC-CCG-AAG-CCT-GTC3' (SEQ ID NO:48)
TRV015: 5'ATC-CTG-AAA-GAC-CCG-AAG-CCT-GTC3' (SEQ ID NO:49)
TRV017: 5'GTC-ATA-AAA-AAC-ATC-TGG-TCC-TGG-TAA-G3' (SEQ ID NO:50)
for *Ureaplasma urealyticus*
UU003: 5'ATT-TCC-TAT-CTT-AGC-GTT-TCT-TCC3' (SEQ ID NO:51)
UU004: 5'CCA-CCT-GTC-ATA-TTG-TTA-ACC-TCA3' (SEQ ID NO:52)
for *Universal Probes*
UP007: 5'GTA-TTA-CCG-CGG-CTG-CTG3' (SEQ ID NO:53)
UP033: 5'GAA-TTA-CCG-CGG-CTG-CTG-G3' (SEQ ID NO:54)
UP028: 5'CGA-CGG-GCG-GTG-TGT-ACA-A3' (SEQ ID NO:55)
UP041: 5'CTG-CTG-CCT-CCC-GTA-GGA-GT3' (SEQ ID NO:56)
UP053: 5'GGA-ATT-ACC-GCG-GCT-GCT-GGC3' (SEQ ID NO:57)
UP055: 5'GGA-ATT-ACC-GCG-GCT-GCT-GGC-ACC3' (SEQ ID NO:58)
UP056: 5'GCT-GGA-ATT-ACC-GCG-GCT-GCT-GGC-ACC3' (SEQ ID NO:59)

In certain sequence, "N" is A, C, G or T. In addition, the sequences can contain up to 5 "N" nucleotides at the 5' and/or the 3' end thereof.

A summary of oligonucleotide probe specificity and utility in sandwich assay is presented in the following table:

| OLIGONUCLEOTIDE PROBE | FILTER HYBRIDIZATION SPECIFICITY[1] | SANDWICH ASSAY[2] |
|---|---|---|
| PB002 | Species-specific | Yes |
| CAL015 | Yeast-specific | Yes |
| CAL020 | Yeast-specific | Yes |
| CT003 | Species-specific | Yes |
| CT005 | Species-specific | Yes |
| GV009 | Species-specific | Yes |
| GV015 | Species-specific | Yes |
| GV017 | n.d. | Yes |
| GV018 | n.d. | Yes |
| GV019 | n.d. | Yes |
| GV020 | n.d. | Yes |
| MSP003 | Species-specific for *M. mulieris* | Yes |
| MH002 | Species-specific | Yes |
| MH004 | Species-specific | Yes |
| NG003 | Neisseria-specific | Yes |
| NG004 | Neisseria-specific | Yes |
| NG007 | Species-specific | Yes |
| NG008 | Species-specific | Yes |
| TRV015 | Species-specific | Yes |
| TRV017 | Species-specific | Yes |
| UU003 | Species-specific | Yes |
| UU004 | Species-specific | Yes |
| UP053 | n.d. | Yes |
| UP054 | n.d. | n.d. |
| UP055 | n.d. | n.d. |
| UP056 | n.d. | Yes |

Abbreviations: n.d.—not determined

1. Hybridization of oligonucleotide probe to a panel of nucleic acid from at least 70 organisms/cell culture lines. Conventional slot blot (filter hybridization) methods using $^{32}$P-labelled oligonucleotide probes were employed. Each slot contained 0.1–0.3 µg of the panel nucleic acid. Hybridization was in 0.6M NaCl/30% formamide. Cross reaction by the panel nucleic acid was defined as a signal intensity equivalent to that observed for the complementary nucleic acid of the oligonucleotide probe.

2. The target-specific oligonucleotide probe was attached to a nylon solid support (membrane or bead). Target nucleic acid was hybridized to the capture oligonucleotide probe and detected using a streptavidin horse radish peroxidase signal system (See, Example 1). The oligonucleotide probe was determined to be functional in a sandwich assay if the equivalent of at least $10^8$ organisms were detected.

Poly(ethyleneimine) may be purchased from Polysciences (Warrington, Pa.).

Burnished or unpolished nylon beads may be purchased from Precision Ball Company (Chicago, Ill.) and The Hoover Group (Sault St. Marie, Mich.).

Triethyloxonium tetrafluoroborate, hexanediamine, phenylenediamine, succinic anhydride and N-methyl-pyrrolidone, Cibacron Brilliant Red, Cibacron Brilliant Yellow, Mordant Orange, Fast Blue BB, Reactive Blue 2, Mordant Brown 4, and Reactive Black may be purchased from Aldrich Chemical (Milwaukee, Wis.).

N-succinimidyl 4-(iodoacetamido)-benzoate (SLAB) and Tween® 20 may be purchased from Pierce (Rockford, Ill.).

Guanidinium thiocyanate (GuSCN) may be purchased from Kodak (Rochester, N.Y.).

PROCEDURES

Oligonucleotide synthesis

Oligonucleotides complementary to conserved regions or hypervariable regions of the 16S ribosomal RNA of *G. vaginalis*, *Trichomonas vaginalis*, or *Candida albicans* are synthesized using phosphoramidite chemistry utilizing an ABI 380B, a Milligen 7500 automated DNA synthesizer, or a similar instrument. The oligonucleotides are prepared using the standard phosphoramidite chemistry supplied by the vendor or H-phosphonate chemistry. Appropriately blocked dA, dG, dC, and dT phosphoramidites are commercially available in these forms, and synthetic nucleosides may readily be converted to the appropriate form. Oligonucleotides are purified by adaptations of standard methods. Oligonucleotides with 5'-trityl groups are chromatographed on HPLC using a 12 µm, 300 ÅA Rainin (Woburn, Mass.) Dynamax C-8 4.2×250 mm reverse phase column using a gradient of 15% to 55% MeCN in 0.1N Et$_3$NH$^+$OAc$^-$, pH 7.0, over 20 minutes. When detritylation is performed, the oligonucleotides are further purified by gel exclusion chromatography. Analytical checks for the quality of the oligonucleotides are conducted with a Toso-Haas DEAE-NPR column at alkaline pH and by polyacrylamide gel electrophoresis (PAGE).

Preparation of a polymer-coated nylon bead 25,000 3/32 inch diameter unpolished nylon beads are placed in a flask containing 1800 mL of 100% anhydrous N-methyl-pyrrolidone and mixed for 5 minutes at ambient temperature. 200 mL of 1 molar triethyloxonium tetra-fluoroborate in dichloromethane are added and the mixture is stirred for 30 minutes at ambient temperature. The beads are then decanted and washed quickly with four 500 mL changes of 100% N-methyl-pyrrolidone. The beads are then transferred to a solution consisting of 3% (w/v) 10,000 MW poly(ethyleneimine), prepared from a 30% aqueous solution of poly(ethyleneimine), in N-methyl-pyrrolidone and stirred for 12 to 24 hours at ambient temperature. The beads are washed with 2000 mL N-methyl-pyrrolidone, 1000 mL SDS/FW and finally 10×2 liter distilled water. The beads are then dried under high vacuum for 4 to 5 hours without the use of heat. The amine content of the beads may be determined by reaction with picrylsulfonic acid.

Preparation of cyanuric chloride-derived oligonucleotides 10 to 1000 µg of 5'-amine-linked oligonucleotide spiked with a small amount of the same oligonucleotide labelled at its 3' end with $^{32}P$ are treated with an excess of recrystallized cyanuric chloride in 10% (w/v) N-methyl-pyrrolidone in an alkaline buffer (pH 8.3 to 8.5, preferably) at ambient temperature for 30 to 120 minutes. The final reaction conditions are 0.15M sodium borate at pH 8.3, 2 mg/mL recrystallized cyanuric chloride and 500 µg/mL appropriate aminohexyl oligonucleotide. The unreacted cyanuric chloride is removed by size exclusion chromatography on a G-50 Sephadex® column (Pharmacia, Uppsala, Sweden).

Cyanuric chloride-derived oligonucleotides and poly(ethyleneimine) coated-nylon beads (described above) are placed in a volume of 0.1M sodium borate, pH 8.3 equal to the volume of the beads at 4° C. The purified cyanuric chloride-derived oligonucleotide is then added to the beads, and the mixture is vigorously agitated at ambient temperature for 60 minutes. The beads are then washed twice with 0.1M sodium borate (pH 8.3). Succinic anhydride is then added at a concentration of 10 mg/mL in 90% (w/v) N-methyl-pyrrolidone and 10% (w/v) 1M sodium borate (pH 8.3) having a volume three times that of the volume of the beads. The reaction is allowed to proceed for 1 hour at ambient temperature. The beads are then washed 3 times with 250 mL of 100% (v/v) N-methyl-pyrrolidone, twice with distilled water, 5 times with 250 mL SDS/FW and then 4 times with 1 liter of distilled water. Beads are stored dry or in 25 mM EDTA. Radio-activity per bead may be determined by liquid scintillation counting, allowing the amount of capture oligo-nucleotide per bead to be calculated.

Lysis of bacteria and hybridization conditions $1 \times 10^8$ G. vaginalis cells are incubated with 100 µl of Proteinase K lysis solution for 20 minutes at about 65° C. This preparation is then combined with 150 µl 5M GuSCN. Five to eight 5-fold serial dilutions are made of the starting lysate. Biotinylated probe is added to the lysates to a final concentration of 100 ng/ml. The solutions are then incubated with the derived nylon beads (covalently immobilized with about 0.1 µg of G. vaginalis oligonucleotide probe (capture probe)) for about 10 minutes to 1 hour at ambient temperature with mild agitation. The solid supports are then washed two times with SDS/FW. Streptavidin/HRP conjugate is added to a final concentration of 1 µg/mL (based on streptavidin) in SDS/FW and incubated about 5 to 15 minutes at ambient temperature with mild agitation. The beads are washed three times with SDS/FW and then once with CAP buffer. The beads are combined with 0.3 mL of 4-methoxy-naphthol substrate solution (as described above), and the reaction is allowed to proceed for 15 minutes at ambient temperature. At this stage of the procedure, the capture probe bead will become colored if G. vaginalis nucleic acid is detected. The beads are then quickly washed once with SDS/FW, once with distilled water and allowed to air dry in the dark.

Quantitative determination of the extent of hybridization (capture of target nucleic acid) using insoluble substrates for either horseradish peroxidase or alkaline phosphatase After the completion of the sandwich assay on the solid support, herein 3/32 inch nylon beads, and the deposition of the insoluble, colored substrate product onto the surface of the bead by either HRP or alkaline phosphatase, the quantity of target nucleic acid captured is determined by fluorescence quenching. The beads are dried for 15 to 30 minutes at ambient temperature and then individually placed in a round-bottom, opaque white microtiter plate (Dynatek Laboratories, Chantilly, Va.). The beads are then read using a fluorometer (Fluoroskan II, Flow Laboratories, McLean, Va.) or equivalent instrument, in which excitation is at 350 nm and emission is at 456 nm. The beads possess an intrinsic fluorescence of about 800 RFUs, and the presence of the colorimetric substrate product effectively quenches the intrinsic fluorescence. Lower indicated fluorescences correlate with greater quantities of captured target nucleic acid. Alternatively, quantitation may be accomplished by measuring light reflected off of the beads using an image analyzer or a reflectance spectrophotometer.

Example 1

Example 1 describes the quantitation of signal in a typical sandwich assay format, in which a target nucleic acid is sequestered and then detected using a colorimetric insoluble enzymatic product obtained using a horseradish peroxidase system. The colored product (i.e., results) may be evaluated by measuring quenching of the natural fluorescence of the bead.

1 mg/mL proteinase K lysis solution is used to lyse $1 \times 10^8$ G. vaginalis cells in 100 µl volumes for 20 minutes at about 65° C. The lysate is adjusted to 3M GuSCN by adding 1.5 volumes of 5M GuSCN. A biotinylated 24-mer oligonucleotide probe complementary to conserved regions of bacterial 16S rRNA (signal probe) is added to a final concentration of 100 ng/ml.

5-fold serial dilutions of the lysates are made using 3M GuSCN hybridization solution containing the biotinylated signal oligonucleotides. Each dilution (200 µl) is then incubated for 30 minutes at ambient temperature with 3 white nylon beads having 0.1 µg of G. vaginalis-specific oligonucleotide probe (capture probe) covalently immobilized thereon. The solid supports are washed twice with SDS/FW at ambient temperature and then incubated with 1–2 µg/mL of streptavidin/horseradish peroxidase (SA/HRP) conjugate in SDS/FW for 5 minutes at ambient temperature. The solid supports are washed with SDS/FW, and then the presence of peroxidase is determined by incubating the beads for about 10–30 minutes with the HRP substrate solution (4MN) to form an insoluble blue product. The beads are then washed once with SDS/FW, wicked dry, and placed in a white, round bottom 96-well microtiter plate (Dynatek Laboratories, Chantilly, Va.). The beads are read using a fluorometer (Fluoroskan II, Flow Laboratories, McLean, Va.) in which excitation is at 350 nm and emission is at 456 nm. Results of such testing will show a decrease in RFUs with an increase in bacterial cell number.

Example 2

Example 2 describes the quantitation of signal in a typical sandwich assay format, in which a target nucleic acid is sequestered and then detected using a colorimetric insoluble enzymatic product obtained using an alkaline phosphatase system.

Proteinase K lysis solution is used to lyse $1 \times 10^8$ G. vaginalis cells in 250 µl volume at about 65° C. for 20 minutes. The lysate is adjusted to 3M GuSCN by the addition of 1.5 volumes of 5M GuSCN. A biotinylated 24-mer oligonucleotide probe complementary to conserved regions of bacterial 16S rRNA (signal probe) is added to a final concentration of 100 ng/ml.

5-fold serial dilutions of the lysates are made using 3M GuSCN hybridization solution containing the biotinylated signal oligonucleotides. Each solution is then incubated for 30 minutes at ambient temperature with 3 nylon beads having 0.1 µg of G. vaginalis-specific oligonucleotide probe (capture probe) covalently immobilized thereon. The solid supports are then washed twice with SDS/FW at ambient temperature and incubated with 10 ng/mL of streptavidin/ alkaline phosphatase (SA/AP) conjugate in APB buffer for 5 minutes at ambient temperature. The solid supports are washed with APB buffer. The presence of alkaline phosphatase may be determined by incubating the beads with the TMNZ substrate solution for 1–4 hours to form an insoluble formazan product. The beads are then washed once with SDS/FW, wicked dry, and placed in a white, round-bottom 96-well microtiter plate (Dynatek Laboratories, Chantilly, Va.). The beads are then read using a fluorometer (Fluoroskan II, Flow Laboratories, McLean, Va.) in which excitation is at 350 nm and emission is at 456 nm. Results of such testing will show a decrease in RFUs with an increase in bacterial cell number.

Example 3

Example 3 demonstrates the use of nylon solid supports in a sandwich assay format, in which a target nucleic acid is sequestered and then detected using an assay format based on detecting a fluorescent product in the presence of beads in a microtiter well embodiment.

Proteinase K lysis solution is used to lyse $1 \times 10^8$ G. vaginalis cells in 100 µl volumes at about 65° C. for 20 minutes. The lysate is adjusted to 3M GuSCN by the addition of 1.5 volumes of 5M GuSCN. A biotinylated 24-mer oligonucleotide probe complementary to conserved regions of bacterial 16S rRNA (signal probe) is added to a final concentration of 100 ng/ml.

5-fold serial dilutions of the lysates are made using 3M GuSCN hybridization solution containing the biotinylated signal oligonucleotides. Each solution is then incubated for 30 minutes at ambient temperature with 2 black nylon beads prepared by The Hoover Group (Sault St. Marie, Mich.) and 2 natural colored nylon beads, each having 0.1 µg of G. vaginalis-specific oligonucleotide probe (capture probe) covalently immobilized thereon. The solid supports are washed with SDS/FW at ambient temperature, followed by washing with 0.1% (v/v) Tweens® 20, 1 mM $MgCl_2$, 0.01M Tris-HCl, pH 8.0 (APB) and incubation with 0.4 µg/mL of streptavidin/alkaline phosphatase (SA/AP) conjugate in APB for 5 minutes at ambient temperature. The solid supports are then washed 5 times with APB, once with TMNZ, and then the presence of alkaline phosphatase may be determined by incubating the nylon beads individually with 150 µl of 0.5 mM 4-methyl-umbelliferyl phosphate (4-hydroxymethyl coumarin) in black microtiter well strips (Dynatek, Laboratories, Chantilly, Va.). Incubation is for 30 minutes at 37° C. The plates are then directly read using a Fluoroskan II fluorometer (Flow Laboratories, McLean, Va.) using an excitation wavelength of 360 nm and an emission wavelength of 456 nm.

As a result of the very high intrinsic fluorescence associated with the virgin (natural colored) nylon beads (800–900 RFUs), a higher level of cells (target nucleic acid) will be detected using the black nylon beads, as compared to the natural colored nylon bead solid supports, when the quantitation is conducted in the presence of the beads. The black nylon beads, which possess a decreased intrinsic fluorescence, will allow the sensitive detection of G. vaginalis 16S rRNA using a fluorescence-based signal system. A control in which the natural colored bead is physically removed from the solution is read, and is expected to indicate the same level of detection of G. vaginalis as when the solution is read in the presence of the black bead.

Example 4

Example 4 describes the coloring or dying of ³⁄₃₂nd inch nylon beads with a multiplicity of dyes, and the resultant reduction of the intrinsic fluorescence of the nylon bead.

Approximately 500 mg of Mordant Red, Reactive Blue 2, Mordant Brown 4, Cibacron Brilliant Red, Cibacron Brilliant Yellow, Reactive Black, or Mordant Orange were dissolved in 50 mL of 50% (v/v) N-methyl-pyrrolidone and 0.2M sodium borate (pH 8.3) and incubated with 1000 ³⁄₃₂nd inch nylon beads for 24 hours at ambient temperature and 1 hour at about 65° C. The beads were then washed with 10 changes of 50 mL of 100% N-methyl-pyrrolidone and 5 changes of 50 mL distilled water. The beads were then dried under high vacuum for 25 hours. Eight beads from each color group were then placed in a round-bottomed, white microtiter plate.

The plates were then directly read using a Fluoroskan II fluorometer (Flow Laboratories, McLean, Va.) using an excitation wavelength of 360 nm and an emission wavelength of 456 nm. The results are shown in Table 2 below.

TABLE 1

| DYED BEADS AND FLUORESCENT SIGNAL | |
|---|---|
| Color | RFUs |
| Native (white) | 2000 |
| Mordant Brown | 3.5 |
| Cibacron Red | 110 |
| Cibacron Yellow | 130 |
| Reactive Black | 2.5 |
| Fast Blue BB | 10 |
| Mordant Orange | 30 |
| Reactive Blue | 3.0 |

Coloring the nylon bead significantly reduced the intrinsic fluorescence of the nylon bead, thereby rendering the beads compatible with fluorescence-based assays when dyed with Mordant Brown, Reactive Black, Fast Blue BB, and Reactive Blue.

Example 5

Example 5 illustrates the various lysis methods which can be used to release nucleic acid from the target microorganism. The first method, designated (1), involves direct immersion of the sample in 3M guanidinium thio-cyanate (GuSCN). The second method (2) requires heating to about 65° C. in 1 mg/mL proteinase K, followed by the addition of GuSCN to a final concentration of 3M. The third method (3) requires heating at 85° C. in a buffered solution containing detergents, followed by addition of GuSCN to a final concentration of 3M. Table 1 set forth below summarizes the results obtained when exemplary lysis reagents were incubated with the indicated organisms in the presence of patient samples.

TABLE 2

| | LYSIS REAGENTS | | |
|---|---|---|---|
| Organism | (1) | (2) | (3) |
| Candida | – | + | + |
| Candida, spiked[a] | – | + | + |
| Gardnerella | –/+ | + | + |
| Gardnerella, spiked[a] | – | + | + |
| Trichomonas | + | + | + |
| Trichomonas, spiked[a] | + | – | + |

[a]"Spiked" means a swab was taken from a BV-negative woman, and about $5 \times 10^7$ cultured organisms were placed directly onto the swab. The swab is then processed as if it were a patient sample.

A plus sign indicates successful detection of target nucleic acid in the presence of vaginal fluid samples. Using these reagents, patient samples are collected into proteinase K followed by GuSCN addition (method (2)) for *Candida albicans* and *G. vaginalis* detection, and into 3M GuSCN (method (1)) for *Trichomonas vaginalis* detection. Alternatively, two patient samples are collected simultaneously, or one patient sample would be divided into aliquots, and incubated in 5M GuSCN and 1 mg/mL proteinase K, respectively. The two solutions are then mixed to a final GuSCN concentration of 3M. The sandwich assay is then performed on this mixture. Still another alternative involves the identification and use of a lysis reagent useful for the release of nucleic acid from all organisms of interest (method 3, described above). The components of the buffered detergent solution, heating temperature, and time of heating may be adjusted for each organism individually or for the organisms in combination. From the foregoing, it is apparent that method 3 readily releases nucleic acid from the microorganisms of interest without the need for enzymes or other complicated procedures.

Example 6

Example 6 illustrates the correlation between the diagnostic criteria employed in the practice of the present invention and conventional BV diagnostic techniques.

Vaginal washes were collected from 43 women determined to be positive for BV by standard clinical criteria and from 70 BV-negative women. These samples were obtained from women visiting the Student Health Clinic at the University of Washington. The women were 92% Caucasian and 8% Asian, with a median age of 23.8 years. Eighty percent of the women tested were unmarried. None were pregnant. Women were determined to be positive for BV by employing the current gold standard diagnostic criteria for the disease. BV-negative women were negative for BV according to the gold standard criteria, and had no obvious signs or symptoms of vaginitis.

Vaginal pH was measured at the time of examination. 3 mL of sterile Hank's balanced salt solution (Flow Laboratories, McLean, Va.) were injected into a patient's vagina and withdrawn to a sterile test tube. 0.25 mL of this vaginal wash were added to 0.5 mL of 5M GuSCN.

Aliquots of 50 and 10 μl of each lysate were diluted to a final volume of 200 μl in 3M GuSCN and loaded onto Nytran filters (Schleicher & Schuell, Keene, N.H.) using a Schleicher & Schuell Minifold II slot blot template. Serial dilutions of purified 16S rRNA from *G. vaginalis* were included on each Nytran filter to provide a standard for quantitation. The filters were baked at 80° C. for 2 hours to lyse the *G. vaginalis* cells and to fix released RNA onto the Nytran filters. The filters were then hybridized with $1 \times 10^6$ cpm/mL of $^{32}$P-labelled GV003, an oligonucleotide specific for *G. vaginalis* 16S rRNA (i.e., it hybridizes selectively with the 16S rRNA of *G. vaginalis* when challenged with over 70 other potentially cross-reacting species of normal vaginal microflora). Hybridization was performed in hybridization/slot blot solution in Seal-a-Meal bags (Dazey). Filters were washed three times with SDS/FW at 55° C. and then were exposed to Kodak X-OMAT AR film, which was developed by standard procedures.

The amount of *G. vaginalis* cells present in each sample was quantitated by comparing the signal intensities obtained from the standards on the filters and those obtained from patient samples. These comparative results could be expressed in terms of cell number, as a result of an additional slot blot experiment. A serial dilution of the same 16S rRNA standard was loaded on a Nytran filter using a Minifold II slot blot template. Serially diluted lysates from three different *G. vaginalis* cultures having known cell numbers (measured by microbiological methods described in the references set forth above) were also loaded on the filter. The slot blots were baked at 80° C. for 2 hours and hybridized with a $^{32}$P-labelled, *G. vaginalis*-specific probe, GV003. Filters were washed and exposed to Kodak X-OMAT AR film, which was developed by standard procedures. Visual examination of the resultant autoradiogram allowed the assignment of a correlation between a given amount of 16S rRNA and a known number of *G. vaginalis* cells.

This correlation was used in combination with autoradiograms of the patient sample slot blots to obtain the cell numbers set forth in Table 3 below.

TABLE 3

| | BV CORRELATES | | |
|---|---|---|---|
| Sample | pH | Slot Blot | + = Gv ≥ $2 \times 10^7$, pH > 4.5 |
| A. BV-Positive Patients: | | | |
| 1 | 5.0 | $<1 \times 10^7$ | – |
| 2 | 5.3 | $2.4 \times 10^7$ | + |
| 3 | 50 | $9.6 \times 10^7$ | + |
| 4 | 5.0 | $3.3 \times 10^8$ | + |
| 5 | 5.0 | $4.2 \times 10^8$ | + |
| 6 | 5.0 | $9 \times 10^8$ | + |
| 7 | 5.0 | $2.4 \times 10^8$ | + |
| 8 | 5.0 | $3 \times 10^8$ | + |
| 9 | 4.7 | $6 \times 10^8$ | + |
| 10 | 5.3 | $3.9 \times 10^8$ | + |
| 11 | 5.0 | $6.6 \times 10^8$ | + |
| 12 | 5.0 | $1.2 \times 10^{10}$ | + |
| 13 | 5.3 | $3.6 \times 10^8$ | + |
| 14 | 5.0 | $6 \times 10^7$ | + |
| 15 | 4.6 | $9.6 \times 10^7$ | + |
| 16 | 5.3 | $9.6 \times 10^7$ | + |
| 17 | 4.7 | $1.5 \times 10^9$ | + |
| 18 | 5.3 | $7.2 \times 10^7$ | + |
| 19 | 4.7 | $3 \times 10^9$ | + |
| 20 | 5.0 | $4.8 \times 10^8$ | + |
| 21 | 4.7 | $3.6 \times 10^8$ | + |
| 22 | 5.0 | $3.6 \times 10^8$ | + |

TABLE 3-continued

BV CORRELATES

| Sample | pH | Slot Blot | + = Gv ≧ 2 × 10⁷, pH > 4.5 |
|---|---|---|---|
| 23 | 5.9 | 1.2 × 10⁹ | + |
| 24 | 5.3 | 4.8 × 10⁸ | + |
| 25 | 5.0 | 1.2 × 10⁸ | + |
| 26 | 4.7 | 9.6 × 10⁷ | + |
| 27 | .5.0 | 1.8 × 10⁹ | + |
| 28 | 5.0 | 1.2 × 10⁸ | + |
| 29 | 5.3 | 3.6 × 10⁸ | + |
| 30 | 5.3 | 7.2 × 10⁸ | + |
| 31 | 5.0 | 2.4 × 10⁸ | + |
| 32 | 5.0 | 1.2 × 10⁸ | + |
| 33 | 4.7 | 2.4 × 10⁷ | + |
| 34 | 5.0 | 1.8 × 10⁸ | + |
| 35 | 5.3 | 3.6 × 10⁷ | + |
| 36 | 5.3 | 1.2 × 10⁸ | + |
| 37 | 5.3 | 4.2 × 10⁷ | + |
| 38 | 5.3 | 8.4 × 10⁷ | + |
| 39 | 5.7 | 5.4 × 10⁷ | + |
| 40 | 5.0 | 3.6 × 10⁸ | + |
| 41 | 5.0 | 1.2 × 10⁸ | + |
| 42 | 5.0 | 4.8 × 10⁸ | + |
| 43 | 5.3 | <1 × 10⁷ | − |
| B. BV-Negative Patients: | | | |
| 1 | 4.7 | 6 × 10⁸ | + |
| 2 | 4.0 | <1 × 10⁷ | − |
| 3 | 4.5 | <1 × 10⁷ | − |
| 4 | 4.0 | <1 × 10⁷ | − |
| 5 | 4.0 | <1 × 10⁷ | − |
| 6 | 4.3 | 3.6 × 10⁷ | − |
| 7 | 4.0 | <1 × 10⁷ | − |
| 8 | 4.0 | <1 × 10⁷ | − |
| 9 | 4.0 | <1 × 10⁷ | − |
| 10 | 4.0 | <1 × 10⁷ | − |
| 11 | 4.0 | <1 × 10⁷ | − |
| 12 | 4.0 | <1 × 10⁷ | − |
| 13 | 4.0 | 1 × 10⁷ | − |
| 14 | 4.0 | 3 × 10⁷ | − |
| 15 | 4.2 | 7.2 × 10⁷ | − |
| 16 | 4.5 | <1 × 10⁷ | − |
| 17 | 4.5 | <1 × 10⁷ | − |
| 18 | 4.0 | 7.2 × 10⁷ | − |
| 19 | 4.0 | <1 × 10⁷ | − |
| 20 | 4.0 | <1 × 10⁷ | − |
| 21 | 4.0 | <1 × 10⁷ | − |
| 22 | 4.0 | <1 × 10⁷ | − |
| 23 | 4.0 | <1 × 10⁷ | − |
| 24 | 4.0 | <1 × 10⁷ | − |
| 25 | 4.0 | <1 × 10⁷ | − |
| 26 | 4.0 | 3 × 10⁷ | − |
| 27 | 4.0 | <1 × 10⁷ | − |
| 28 | 4.0 | 3 × 10⁷ | − |
| 29 | 4.0 | <1 × 10⁷ | − |
| 30 | 4.0 | <1 × 10⁷ | − |
| 31 | 4.0 | <1 × 10⁷ | − |
| 32 | 4.0 | <1 × 10⁷ | − |
| 33 | n.a. | 1.9 × 10⁷ | − |
| 34 | 4.0 | 1.9 × 10⁷ | − |
| 35 | 4.2 | 1.9 × 10⁷ | − |
| 36 | 4.2 | 9.6 × 10⁷ | − |
| 37 | 4.0 | <1 × 10⁷ | − |
| 38 | 4.2 | 9.5 × 10⁷ | − |
| 39 | 4.0 | <1 × 10⁷ | − |
| 40 | 4.2 | 1.9 × 10⁷ | − |
| 41 | 4.2 | 3 × 10⁸ | − |
| 42 | 4.0 | 1.8 × 10⁸ | − |
| 43 | 4.0 | <1 × 10⁷ | − |
| 44 | 4.0 | <1 × 10⁷ | − |
| 45 | 4.0 | <1 × 10⁷ | − |
| 46 | 4.2 | <1 × 10⁷ | − |
| 47 | 4.3 | <1 × 10⁷ | − |
| 48 | 4.0 | <1 × 10⁷ | − |
| 49 | 4.2 | <1 × 10⁷ | − |
| 50 | 4.5 | 2.4 × 10⁹ | − |
| 51 | 4.0 | <1 × 10⁷ | − |
| 52 | 4.0 | 6 × 10⁷ | − |
| 53 | 4.0 | 2 × 10⁷ | − |
| 54 | 4.0 | <1 × 10⁷ | − |
| 55 | 4.0 | <1 × 10⁷ | − |
| 56 | n.a. | <1 × 10⁷ | − |
| 57 | 4.5 | <1 × 10⁷ | − |
| 58 | 4.0 | 1.2 × 10⁸ | − |
| 59 | 4.0 | 3.6 × 10⁷ | − |
| 60 | 4.0 | 3.6 × 10⁷ | − |
| 61 | 4.0 | <1 × 10⁷ | − |
| 62 | 4.0 | <1 × 10⁷ | − |
| 63 | 4.0 | <1 × 10⁷ | − |
| 64 | 4.0 | <1 × 10⁷ | − |
| 65 | 4.0 | <1 × 10⁷ | − |
| 66 | 4.0 | <1 × 10⁷ | − |
| 67 | 4.0 | <1 × 10⁷ | − |
| 68 | 4.0 | <1 × 10⁷ | − |
| 69 | 4.0 | <1 × 10⁷ | − |
| 70 | 4.0 | 1 × 10⁷ | − |

The lower limit of detection for this slot blot analysis was approximately $1 \times 10^7$ G. vaginalis cells, based on the signals obtained with the standards. The results showed a strong correlation between the clinical diagnosis of BV and a concentration of G. vaginalis cells greater than or equal to $2 \times 10^7$ cells/mL vaginal fluid in women with a vaginal pH greater than 4.5. Using the diagnostic criteria of the present invention, BV was detected with a sensitivity of 95.3% and a specificity of 98.6%. Women with trichomoniasis or cervicitis would be expected to exhibit a vaginal pH>4.5, but G. vaginalis cell numbers $<2 \times 10^7$ (i.e., would be diagnosed as BV-negative).

Example 7

Example 7 describes simultaneous detection of Gardnerella vaginalis, Candida species and Trichomonas vaginalis in a complex biological sample, and in particular from a vaginal sample.

Materials

Hybridization I Solution is 83 mM Tris-Cl, pH 7.5; 17 mM EDTA; 8.35% (v/v) formamide; 5M GuSCN; and UP041- polymer, 1.67 µg/ml.

Lysis Solution is 90 mM Tris-Cl, pH 8.0; 10 mM EDTA; 5% (w/v) N-lauroylsarcosine; 0.5% (w/v) SDS; and 0.1% ProClin® (preservative).

Substrate Solution B is 1% (w/v) 4-methoxy naphthol; 0.1% (v/v) acetic acid; and isopropanol.

Hybridization II Solution is 3M GuSCN; 0.3M imidazole; 5% (v/v) formamide; 50 mM Tris-Cl, pH 8.5; 10 mM EDTA; and biotinylated probes capable of hybridizing with Gardnerella vaginalis, Candida species and Trichomonas vaginalis (UP541 [complement of UP041], 1000 µg/ml, Gv; procedural control probe, 1 µg/ml; UP053, 500 µg/ml, Ca; TRV017, 500 µg/ml, Tv).

Assay Wash Solution is 9.1 mM Tris-Cl, pH 8.0; Na-EDTA; 1% (w/v) N-lauroylsarcosine; 1% (w/v) SDS; and 0.1% (w/v) ProClin® (preservative).

Conjugate Solution is streptavidin-horse radish peroxidase conjugate, 1–3 µg SA/ml.

Substrate Solution I is 100 mM Na—$H_2PO_4$, pH 6.5; 12 mM citrate; and 1.8% (v/v) hydrogen peroxide.

Oligonucleotide Probes
for *Prevotella bivia*
5'GGAACACGTTCCCCACTTATCCCC3';
5'TGCCCTAGGTCGATCCTTACGGTC3';
5'GGGATGCTTAATGCTTTCGCTTAG3'; and
5'TACGGTCACGAACTTCAGGCACCC3';
for *Prevotella melaninogenica*
5'GTCATTATCTCTAAATCCTTCCTC3';
5'CAATCACCAGTTTTGCCCTAGGCC3'; and
5'GATCCTTGGGGTCACGGACTTCAG3';
for *Gardnerella vaginalis*
5'CACTCACCCAAAAGGCTTGCTCCC3';
5'GTCCGANACAGAACCCGTGGAATG3';
5'TACACTCACCCAAAAGGCTTGCTGCCC3';
5'GTCCGACACAGAACCCGTGGAATG3';
5'CCCCACATCCAGCGTCCACCG3';
5'GGCCCCACATCCAGCGTCCA3'; and
5'GGCTTGCTGCCCAATCAAAAGCGGTTTAC3';
for *Trichomonas vaginalis*
5'ATC-CTN-AAA-GAC-CCG-AAG-CCT-GTC3'
5'ATC-CTG-AAA-GAC-CCG-AAG-CCT-GTC3'
5'GTC-ATA-AAA-AAC-ATC-TGG-TCC-TGG-TAA-G3'
for *Mycoplasma hominis*
5'GTGATTCTCCACCGACTAATGATC3';
5'CCGACAAGGTACCGTCAGTCTGCA3';
5'CATTTCCTATTGCAAATGTTCTTC3';
5'CCATCTGTCACTCCGATAACCTCC3';
5'CCAGTCCTACCTTAGGCGGTCGCC3';
5'CTGCAATCATTTCTTATTGCAAAT3'; and
5'CTGACAAGGTACCGTCAGTCTGCA3';
for *Mobiluncus curtesii* complex
5'ACCATCAACACAGCCAAAACTGTGCCTT3'
for *Mobiluncus mulieris*
5'ACCATCAACACACCCAAAAGCATGCCTTT3'
for *Neisseria gonorrhoeae*
5'CTCCGTCTCCGGAGGATTCCGCAC3';
5'ATATTGGCAACAGCCTTTTCTTCC3';
5'GCCGCCGATATTGGCAACAGCCTT3';
5'ATATTGGCAACGGCCTTTTCTTCC3';
5'GCCGCCGATATTGGCAACGGCCTT3'; and
5'TGCTTTCCCTCTCAAGACGTATGCG3';
for *Chlamydia trachomatis*
5'ACCGTCTTCTCTTATTCCCAAGCG3'; and
5'TC(AGCT)AGCGGGTATTAACCGTCTTCT3';
for *Ureaplasma urealyticus*
5'ATTTCCTATCTTAGCGTTTCTTCC3'; and
5'CCACCTGTCATATTGTTAACCTCA3';
for Candida species
5'TTCCTCGTTAAGGTATTTACATTG3';
5'CGTTAAGGTATTTACATTGTACTC3';
5'AAGGTATTTACATTGTACTCATTC3';
5'TTGTTCCTCGTTAAGGTATTTACATTGTACTC3'; and
5'GTCAATCCTTATTGTGTCTGGACCTGGT3';
for *Streptococcus agalactiae*
5'TACCGTCACTTGGTAGATTTTCCACTCC3';
5'GATTTTCCACTCCTACCAACGTTCTTCTC3';
5'CCTACCAACGTTCTTCTCTAACAACAGAGC3';
5'GGTAGATTTTCCACTCCTACCAACGTTCTTCTC3'; and
5'GGTAGATTTTCCACTCCTACCAACGTTC3';
for *Streptococcus pyogenes*
5'GATTTTCCACTCCCACCATCATTCTTCTC3';
for Enterobacteriaceae
5'GTCCCCCTCTTTGGTCTTGCGACGTTAT3'; and
5'CATTACTCACCCGTCCGCCACTCGTC3';

Target Oligonucleotide Subsequences
for *Neisseria gonorrhoeae*
5'GUGCGGAAUCCUCCGGAGACGGAG3' (SEQ ID NO:60)
5'GGAAGAAAAGGCUGUUGCCAAUAU3' (SEQ ID NO:61)
5'AAGGCUGUUGCCAAUAUCGGCGGC3' (SEQ ID NO:62)
5'GGAAGAAAAGGCCGUUGCCAAUAU3' (SEQ ID NO:63)
5'AAGGCCGUUGCCAAUAUCGGCGGC3' (SEQ ID NO:64)
for *Mycoplasma hominis*
5'UGCAGACUGACGGUACCUUGUCGG3' (SEQ ID NO:65)
5'GGAGGUUAUCGGAGUGACAGAUGG3' (SEQ ID NO:66)
5'AUUUGCAAUAAGAAAUGAUUGCAG3' (SEQ ID NO:67)
for *Chlamydia trachomatis*
5'CGCUUGGGAAUAAGAGAAGACGGU3' (SEQ ID NO:68)
5'AGAAGACGGUUAAUACCCGCU(AGCU)GA3' (SEQ ID NO:69)
for Candida species
5'CAAUGUAAAUACCUUAACGAGGAA3' (SEQ ID NO:70)
5'GAGUACAAUGUAAAUACCUUAACG3' (SEQ ID NO:71)
5'GAAUGAGUACAAUGUAAAUACCUU3' (SEQ ID NO:72)

Procedure

Patient samples are collected from symptomatic females presenting with vaginal complaint. The patients preferably have not been treated with anti-bacterial or anti-fungal medication within the week prior to sample collection, and preferably have not douched within 24 hours of sample collection.

A sterile dacron swab with a pre-scored handle was used to obtain vaginal fluid samples by twisting or rolling the swab against the vaginal wall two or three times, ensuring that the entire circumference of the swab touched the vaginal wall. The swab was then placed in a sample collection tube, the pre-scored handle of the swab was broken, and the tube was capped. The unlubricated speculum was removed from the patient, and the vaginal pH was determined by touching a pH indicator strip to the speculum.

The swab/sample was either: (1) transported at room temperature for immediate processing and analysis; (2) held at 0° C. to 8° C. for four hours prior to processing and analysis; or (3) held at room temperature for one hour prior to processing and analysis. To initiate processing, 0.3 mL of Lysis Solution was added to the swab/sample, which was then swirled or agitated in the Lysis Solution for about 10–15 seconds. The tube containing the swab and Lysis Solution was heated at 85° C. for about 5 minutes (4–8 minutes). 0.45 mL Hybridization I Solution was added to the sample, and the contents of the tube were mixed by flicking about 10 times. At this point, samples may be stored for up to 24 hours at room temperature.

The swab contents were expressed by twirling the swab against the side of the tube. The solution remaining in the tube was then processed on an semi-automated instrument. The sample solution was filtered into the first well of a 7-well reagent cassette. A dipstick containing five beads (i.e. a procedural control, a negative control, *Gardnerella vaginalis*-specific capture probe GV009, Candida species-specific capture probe CAL015, and *Trichomonas vaginalis*-specific capture probe TRV015) was inserted into Well 1. Substrate Solution B (0.06 ml) was added to Well 7 of the reagent cassette. The arm of the semi-automated instrument clasped the dipstick, and the dipstick was moved from the first well (sample lysate solution) through the following wells: Well 2=Hybridization II Solution; Well 3=Assay Wash Solution; Well 4=Conjugate Solution; Wells 5 and 6=Assay Wash Solution; and Well 7=Substrate Solution I. The presence of blue color on a test bead at the end of automated sample processing was indicative of a detectable level of nucleic acid from that target organism. For assay validity, the procedural control bead must turn blue and the negative control bead must remain colorless. The intensity of the blue color on a bead was estimated using an image analyzer.

Example 8

Example 8 describes a preferred method for simultaneous detection of *Gardnerella vaginalis*, Candida species, and *Trichomonas vaginalis* in a complex biological sample, and in particular from a vaginal sample.

Materials

Hybridization I solution is 83 mM Tris-Cl, pH7.5; 17 mM EDTA; 8.35% (v/v) formamide; 5M GnSCN; UP041-polymer, 1.67 µg/ml; and UP053-polymer, 1.67 µg/ml.

Lysis Solution is 50 mM glycine, 10 mM EDTA, 5% (w/v) N-lauroylsarcosine, 0.5% (w/v) SDS, and 0.1% Pro-Clin® (preservative), pH 11.

Substrate Solution B (now called Substrate Solution S) is the same as in Example 7.

Hybridization II Solution is 3M GnSCN; 0.3M imidazole; 5% (v/v) formamide; 50 mM Tris-Cl, pH 8.5; 10 mM EDTA; and biotinylated probes capable of hybridizing with *Gardnerella vaginalis*, Candida species, and *Trichomonas vaginalis* (UP541 [complement of UP041], 1000 µg/ml, Gv; procedural control probe, 0.3 µg/ml; UP553 [complement of UP053], 1000 µg/ml, Ca; Trv017, 500 µg/ml, Tv).

Assay Wash Solution, Conjugate Solution, and Substrate Solution I are the same as in Example 7.

Oligonucleotide Probes

CAL015
GV015
TRV015
UP053-polymer
TRV017
UP041-polymer
UP553 (complement of UP053)
UP541 (complement of UP041)

Procedure

The same as in Example 7, except:

1) Vaginal scrapings or pelleted vaginal washes can be used as alternatives to the vaginal swab sample.
2) A 10-minute heating at 85° C. replaces the 5-minute heating at 85° C.

Example 9

Example 9 describes a preferred method for simultaneous detection of *Gardnerella vaginalis*, *Trichomonas vaginalis*, and Group B Streptococci in a complex biological sample, and in particular, from a vaginal sample.

Materials

Hybridization I solution is 83 mM Tris-Cl, pH 7.5; 17 mM EDTA; 8.35% (v/v) formamide; 5M GnSCN; 2% N-lauroylsarcosine; UP041-polymer, 1.67 µg/ml; and UP056-polymer, 3.34 µg/ml, pH 7.2–7.8.

Lysis Solution is 50 mM Tris-Cl, 10 mM EDTA, 2% (w/v) N-lauroylsarcosine, 0.5% (w/v) SDS, and 0.1% ProClin® preservative), pH 7.5

Substrate Solution B (now called Substrate Solution S) is the same as in Example 7.

Hybridization II Solution is 3M GnSCN; 0.3M imidazole; 5% (v/v) formamide; 50 mM Tris-Cl, pH 8.5; 10 mM EDTA; and biotinylated probes capable of hybridizing with *Gardnerella vaginalis*, *Trichomonas vaginalis*, and Group B streptococci (UP541 [complement of UP041]; 1 µg/ml; Procedural control probe, 0.3 µg/ml; Trv017, 500 µg/ml; and UP557 [complement of UP056]; 1 µg/ml.

Oligonucleotide Probes:

GV009
SA005
TRV015
TRV017
UP557 (complement of UP056)
UP056-polymer
UP041-polymer
UP541 (complement of UP041)
PA505 (positive control) 5'CTT-GCA-GAT-GGT-GGA-AGG-TAT-GTC3'

Procedure

The same as in Example 7, except:

1) Vaginal scrapings or pelleted vaginal washes can be used as alternatives to the vaginal swab sample.
2) A 10-minute heating at 85° C. replaces the 5-minute heating at 85° C.

The foregoing is offered primarily for purposes of illustration. It will be readily apparent to those skilled in the art that the operating conditions, materials, procedural steps and other parameters of the systems described herein may be further modified or substituted in various ways without departing from the spirit and scope of the invention.

---

What is claimed is:

1. A kit for simultaneously detecting *Gardnerella vaginalis*, *Candida albicans* and *Trichomonas vaginalis*, comprising:

(a) a dipstick comprising a nonporous solid support having at least three capture oligonucleotide-coated beads attached thereto, wherein a first bead specifically hybridizes with *Gardnerella vaginalis* nucleic acid wherein the capture oligonucleotide is selected from the group consisting of SEQ ID NOS: 18–26, a second bead specifically hybridizes with *Candida albicans* nucleic acid wherein the capture oligonucleotide is SEQ ID NO: 13, and a third bead specifically hybridizes with *Trichomonas vaginalis* nucleic acid wherein the capture oligonucleotide is selected from the group consisting of SEQ ID NOS: 48–50

(b) a lysis solution capable of releasing nucleic acid from *Gardnerella vaginalis*, *Candida albicans* and *Trichomonas vaginalis* microorganisms; and (c) a container having therein at least three signal oligonucleotides, wherein a first signal oligonucleotide specifically hybridizes with *Gardnerella vaginalis* nucleic acid, a second signal oligonucleotide specifically hybridizes with *Candida albicans* nucleic acid, and a third signal oligonucleotide specifically hybridizes with *Trichomonas vaginalis* nucleic acid.

2. The kit in accordance with claim 1 further comprising a regent cassette or multi-cavity reagent container.

* * * * *

SEQUENCE LISTING ( 1 ) GENERAL INFORMATION:

( i i i ) NUMBER OF SEQUENCES: 72

( 2 ) INFORMATION FOR SEQ ID NO:1:

( i ) SEQUENCE CHARACTERISTICS:
( A ) LENGTH: 24 base pairs
( B ) TYPE: nucleic acid (C) STRANDEDNESS: single
(D) TOPOLOGY: linear (ii) MOLECULE TYPE: DNA (ix) FEATURE:
 (A) NAME/KEY: misc_feature
 (B) LOCATION: 1..24
 (D) OTHER INFORMATION: /standard_name= "PB002"

(xi) SEQUENCE DESCRIPTION: SEQ ID NO:1:

GGAACACGTT CCCCACTTAT CCCC 24

(2) INFORMATION FOR SEQ ID NO:2:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: DNA (ix) FEATURE:
 (A) NAME/KEY: misc_feature
 (B) LOCATION: 1..24
 (D) OTHER INFORMATION: /standard_name= "PB004"

(xi) SEQUENCE DESCRIPTION: SEQ ID NO:2:

TGCCCTAGGT CGATCCTTAC GGTC 24

(2) INFORMATION FOR SEQ ID NO:3:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: DNA (ix) FEATURE:
 (A) NAME/KEY: misc_feature
 (B) LOCATION: 1..24
 (D) OTHER INFORMATION: /standard_name= "PB006"

(xi) SEQUENCE DESCRIPTION: SEQ ID NO:3:

GGGATGCTTA ATGCTTTCGC TTAG 24

(2) INFORMATION FOR SEQ ID NO:4:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: DNA (ix) FEATURE:
 (A) NAME/KEY: misc_feature
 (B) LOCATION: 1..24
 (D) OTHER INFORMATION: /standard_name= "PB008"

(xi) SEQUENCE DESCRIPTION: SEQ ID NO:4:

TACGGTCACG AACTTCAGGC ACCC 24

(2) INFORMATION FOR SEQ ID NO:5:

(i) SEQUENCE CHARACTERISTICS:
 (A) LENGTH: 24 base pairs
 (B) TYPE: nucleic acid (C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "BM003"

(xi) SEQUENCE DESCRIPTION: SEQ ID NO:5:

GTCATTATCT CTAAATCCTT CCTC    24

(2) INFORMATION FOR SEQ ID NO:6:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "BM005"

(xi) SEQUENCE DESCRIPTION: SEQ ID NO:6:

CAATCACCAG TTTTGCCCTA GGCC    24

(2) INFORMATION FOR SEQ ID NO:7:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "BM006"

(xi) SEQUENCE DESCRIPTION: SEQ ID NO:7:

GATCCTTGGG GTCACGGACT TCAG    24

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "CAL001"

(xi) SEQUENCE DESCRIPTION: SEQ ID NO:8:

TTCCTCGTTA AGGTATTTAC ATTG    24

(2) INFORMATION FOR SEQ ID NO:9:

(i) SEQUENCE CHARACTERISTICS:
(A) LENGTH: 24 base pairs
(B) TYPE: nucleic acid

```
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..24
            ( D ) OTHER INFORMATION: /standard_name= "CAL002"

( x i ) SEQUENCE DESCRIPTION: SEQ ID NO:9:

CGTTAAGGTA TTTACATTGT ACTC                                                      24

( 2 ) INFORMATION FOR SEQ ID NO:10:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..24
            ( D ) OTHER INFORMATION: /standard_name= "CAL003"

( x i ) SEQUENCE DESCRIPTION: SEQ ID NO:10:

AAGGTATTTA CATTGTACTC ATTC                                                      24

( 2 ) INFORMATION FOR SEQ ID NO:11:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..27
            ( D ) OTHER INFORMATION: /standard_name= "CAL004"

( x i ) SEQUENCE DESCRIPTION: SEQ ID NO:11:

TTCCTCGTTA AGGTATTTAC ATTGTAC                                                   27

( 2 ) INFORMATION FOR SEQ ID NO:12:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..32
            ( D ) OTHER INFORMATION: /standard_name= "CAL015"

( x i ) SEQUENCE DESCRIPTION: SEQ ID NO:12:

TTGTTCCTCG TTAAGGTATT TACATTGTAC TC                                             32

( 2 ) INFORMATION FOR SEQ ID NO:13:

( i ) SEQUENCE CHARACTERISTICS:
            ( A ) LENGTH: 28 base pairs
            ( B ) TYPE: nucleic acid
```

( C ) STRANDEDNESS: single
       ( D ) TOPOLOGY: linear ( i i ) MOLECULE TYPE: DNA ( i x ) FEATURE:
       ( A ) NAME/KEY: misc_feature
       ( B ) LOCATION: 1..28
       ( D ) OTHER INFORMATION: /standard_name= "CAL020"

( x i ) SEQUENCE DESCRIPTION: SEQ ID NO:13:

GTCAATCCTT ATTGTGTCTG GACCTGGT                                        28

( 2 ) INFORMATION FOR SEQ ID NO:14:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: DNA ( i x ) FEATURE:
       ( A ) NAME/KEY: misc_feature
       ( B ) LOCATION: 1..24
       ( D ) OTHER INFORMATION: /standard_name= "CTO03"

( x i ) SEQUENCE DESCRIPTION: SEQ ID NO:14:

ACCGTCTTCT CTTATTCCCA AGCG                                            24

( 2 ) INFORMATION FOR SEQ ID NO:15:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: DNA ( i x ) FEATURE:
       ( A ) NAME/KEY: misc_feature
       ( B ) LOCATION: 1..24
       ( D ) OTHER INFORMATION: /standard_name= "CTO05"

( x i ) SEQUENCE DESCRIPTION: SEQ ID NO:15:

TCNAGCGGGT ATTAACCGTC TTCT                                            24

( 2 ) INFORMATION FOR SEQ ID NO:16:

( i ) SEQUENCE CHARACTERISTICS:
       ( A ) LENGTH: 28 base pairs
       ( B ) TYPE: nucleic acid
       ( C ) STRANDEDNESS: single
       ( D ) TOPOLOGY: linear ( i i ) MOLECULE TYPE: DNA ( i x ) FEATURE:
       ( A ) NAME/KEY: misc_feature
       ( B ) LOCATION: 1..28
       ( D ) OTHER INFORMATION: /standard_name= "EC020"

( x i ) SEQUENCE DESCRIPTION: SEQ ID NO:16:

GTCCCCCTCT TTGGTCTTGC GACGTTAT                                        28

( 2 ) INFORMATION FOR SEQ ID NO:17:

( i ) SEQUENCE CHARACTERISTICS:
       ( A ) LENGTH: 26 base pairs
       ( B ) TYPE: nucleic acid (C) STRANDEDNESS: single
(D) TOPOLOGY: linear (ii) MOLECULE TYPE: DNA (ix) FEATURE:
(A) NAME/KEY: misc_feature
(B) LOCATION: 1..26
(D) OTHER INFORMATION: /standard_name= "EC021"

(xi) SEQUENCE DESCRIPTION: SEQ ID NO:17:

CATTACTCAC CCGTCCGCCA CTCGTC 26

(2) INFORMATION FOR SEQ ID NO:18:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "GV003"

(xi) SEQUENCE DESCRIPTION: SEQ ID NO:18:

AGACGGCTCC ATCCCAAAAG GGTT 24

(2) INFORMATION FOR SEQ ID NO:19:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "GV006"

(xi) SEQUENCE DESCRIPTION: SEQ ID NO:19:

CACTCACCCA AAAGGCTTGC TCCC 24

(2) INFORMATION FOR SEQ ID NO:20:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..24
(D) OTHER INFORMATION: /standard_name= "GV008"

(xi) SEQUENCE DESCRIPTION: SEQ ID NO:20:

GTCCGANACA GAACCCGTGG AATG 24

(2) INFORMATION FOR SEQ ID NO:21:

(i) SEQUENCE CHARACTERISTICS:
(A) LENGTH: 24 base pairs
(B) TYPE: nucleic acid (C) STRANDEDNESS: single
(D) TOPOLOGY: linear (i i) MOLECULE TYPE: DNA (i x) FEATURE:
(A) NAME/KEY: misc_feature
(B) LOCATION: 1..24
(D) OTHER INFORMATION: /standard_name= "GV009"

(x i) SEQUENCE DESCRIPTION: SEQ ID NO:21:

GGCCCCACAT CCAGCGTCCA CCGT 24

(2) INFORMATION FOR SEQ ID NO:22:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (i x) FEATURE:
(A) NAME/KEY: misc_feature
(B) LOCATION: 1..27
(D) OTHER INFORMATION: /standard_name= "GV015"

(x i) SEQUENCE DESCRIPTION: SEQ ID NO:22:

TACACTCACC CAAAAGGCTT GCTGCCC 27

(2) INFORMATION FOR SEQ ID NO:23:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (i x) FEATURE:
(A) NAME/KEY: misc_feature
(B) LOCATION: 1..24
(D) OTHER INFORMATION: /standard_name= "GV017"

(x i) SEQUENCE DESCRIPTION: SEQ ID NO:23:

GTCCGACACA GAACCCGTGG AATG 24

(2) INFORMATION FOR SEQ ID NO:24:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:24:

CCCCACATCC AGCGTCCACC G 21

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA ( x i ) SEQUENCE DESCRIPTION: SEQ ID NO:25:

GGCCCCACAT CCAGCGTCCA 20

( 2 ) INFORMATION FOR SEQ ID NO:26:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:26:

GGCTTGCTGC CCAATCAAAA GCGGTTTAC 29

( 2 ) INFORMATION FOR SEQ ID NO:27:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:27:

GTGATTCTCC ACCGACTAAT GATC 24

( 2 ) INFORMATION FOR SEQ ID NO:28:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:28:

CCGACAAGGT ACCGTCAGTC TGCA 24

( 2 ) INFORMATION FOR SEQ ID NO:29:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:29:

CATTTCCTAT TGCAAATGTT CTTC 24

( 2 ) INFORMATION FOR SEQ ID NO:30:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:30:

CCATCTGTCA CTCCGATAAC CTCC 24

( 2 ) INFORMATION FOR SEQ ID NO:31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

CCAGTCCTAC CTTAGGCGGT CGCC         24

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

CTGCAATCAT TTCTTATTGC AAAT         24

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

CTGACAAGGT ACCGTCAGTC TGCA         24

( 2 ) INFORMATION FOR SEQ ID NO:34:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

ACCATCAACA CACCCAAAAG CATGCCTTT         29

( 2 ) INFORMATION FOR SEQ ID NO:35:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

ACCATCAACA CAGCCAAAAC TGTGCCTTT         29

( 2 ) INFORMATION FOR SEQ ID NO:36:

( i ) SEQUENCE CHARACTERISTICS:
        ( A ) LENGTH: 24 base pairs
        ( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:36:

CTCCGTCTCC GGAGGATTCC GCAC                                                      24

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

ATATTGGCAA CAGCCTTTTC TTCC                                                      24

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

GCCGCCGATA TTGGCAACAG CCTT                                                      24

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

ATATTGGCAA CGGCCTTTTC TTCC                                                      24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

GCCGCCGATA TTGGCAACGG CCTT                                                      24

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA ( x i ) SEQUENCE DESCRIPTION: SEQ ID NO:41:

TGCTTTCCCT CTCAAGACGT ATGCG 25

( 2 ) INFORMATION FOR SEQ ID NO:42:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

TACCGTCACT TGGTAGATTT TCCACTCC 28

( 2 ) INFORMATION FOR SEQ ID NO:43:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GATTTTCCAC TCCTACCAAC GTTCTTCTC 29

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CCTACCAACG TTCTTCTCTA ACAACAGAGC 30

( 2 ) INFORMATION FOR SEQ ID NO:45:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

GGTAGATTTT CCACTCCTAC CAACGTTCTT CTC 33

( 2 ) INFORMATION FOR SEQ ID NO:46:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

GGTAGATTTT CCACTCCTAC CAACGTTC 28

( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

GATTTCCAC TCCCACCATC ATTCTTCTC       29

( 2 ) INFORMATION FOR SEQ ID NO:48:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

ATCCTNAAAG ACCCGAAGCC TGTC       24

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

ATCCTGAAAG ACCCGAAGCC TGTC       24

( 2 ) INFORMATION FOR SEQ ID NO:50:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

GTCATAAAAA ACATCTGGTC CTGGTAAG       28

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

ATTTCCTATC TTAGCGTTTC TTCC       24

( 2 ) INFORMATION FOR SEQ ID NO:52:

( i ) SEQUENCE CHARACTERISTICS:
        ( A ) LENGTH: 24 base pairs
        ( B ) TYPE: nucleic acid ( C ) STRANDEDNESS: single
        ( D ) TOPOLOGY: linear ( i i ) MOLECULE TYPE: DNA ( x i ) SEQUENCE DESCRIPTION: SEQ ID NO:52:

CCACCTGTCA TATTGTTAAC CTCA                                                24

( 2 ) INFORMATION FOR SEQ ID NO:53:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

GTATTACCGC GGCTGCTG                                                       18

( 2 ) INFORMATION FOR SEQ ID NO:54:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

GAATTACCGC GGCTGCTGG                                                      19

( 2 ) INFORMATION FOR SEQ ID NO:55:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

CGACGGGCGG TGTGTACAA                                                      19

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CTGCTGCCTC CCGTAGGAGT                                                     20

( 2 ) INFORMATION FOR SEQ ID NO:57:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

GGAATTACCG CGGCTGCTGG C	21

( 2 ) INFORMATION FOR SEQ ID NO:58:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:58:

GGAATTACCG CGGCTGCTGG CACC	24

( 2 ) INFORMATION FOR SEQ ID NO:59:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:59:

GCTGGAATTA CCGCGGCTGC TGGCACC	27

( 2 ) INFORMATION FOR SEQ ID NO:60:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:60:

GUGCGGAAUC CUCCGGAGAC GGAG	24

( 2 ) INFORMATION FOR SEQ ID NO:61:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:61:

GGAAGAAAAG GCUGUUGCCA AUAU	24

( 2 ) INFORMATION FOR SEQ ID NO:62:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:62:

AAGGCUGUUG CCAAUAUCGG CGGC	24

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:63:

GGAAGAAAAG GCCGUUGCCA AUAU    24

( 2 ) INFORMATION FOR SEQ ID NO:64:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:64:

AAGGCCGUUG CCAAUAUCGG CGGC    24

( 2 ) INFORMATION FOR SEQ ID NO:65:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:65:

UGCAGACUGA CGGUACCUUG UCGG    24

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:66:

GGAGGUUAUC GGAGUGACAG AUGG    24

( 2 ) INFORMATION FOR SEQ ID NO:67:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:67:

AUUUGCAAUA AGAAAUGAUU GCAG    24

( 2 ) INFORMATION FOR SEQ ID NO:68:

( i ) SEQUENCE CHARACTERISTICS:
        ( A ) LENGTH: 24 base pairs
        ( B ) TYPE: nucleic acid

```
        ( C ) STRANDEDNESS: single
        ( D ) TOPOLOGY: linear ( i i ) MOLECULE TYPE: RNA ( x i ) SEQUENCE DESCRIPTION: SEQ ID NO:68:

CGCUUGGGAA UAAGAGAAGA CGGU                                              24

( 2 ) INFORMATION FOR SEQ ID NO:69:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:69:

AGAAGACGGU UAAUACCCGC UNGA                                              24

( 2 ) INFORMATION FOR SEQ ID NO:70:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:70:

CAAUGUAAAU ACCUUAACGA GGAA                                              24

( 2 ) INFORMATION FOR SEQ ID NO:71:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:71:

GAGUACAAUG UAAAUACCUU AACG                                              24

( 2 ) INFORMATION FOR SEQ ID NO:72:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:72:

GAAUGAGUAC AAUGUAAAUA CCUU                                              24
```